United States Patent
Liu et al.

(10) Patent No.: US 12,083,534 B2
(45) Date of Patent: Sep. 10, 2024

(54) HIERARCHICAL SILICA LAMELLA FOR MAGNETIC NUCLEIC ACID EXTRACTIONS

(71) Applicant: CIRCULOMICS INC., Baltimore, MD (US)

(72) Inventors: Kelvin Jeng-Fang Liu, Baltimore, MD (US); Jeffrey Michael Burke, Baltimore, MD (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 51 days.

(21) Appl. No.: 17/518,183

(22) Filed: Nov. 3, 2021

(65) Prior Publication Data

US 2022/0055040 A1 Feb. 24, 2022

Related U.S. Application Data

(60) Continuation of application No. 16/917,751, filed on Jun. 30, 2020, now Pat. No. 11,198,135, which is a
(Continued)

(51) Int. Cl.
*B03C 1/01* (2006.01)
*B01D 15/42* (2006.01)
(Continued)

(52) U.S. Cl.
CPC .............. *B03C 1/30* (2013.01); *B01D 15/424* (2013.01); *B03C 1/01* (2013.01); *B03C 1/286* (2013.01);
(Continued)

(58) Field of Classification Search
CPC .............. B03C 1/30; B03C 1/01; B03C 1/286; B03C 1/288; B03C 2201/18; B03C 2201/26;
(Continued)

(56) References Cited

U.S. PATENT DOCUMENTS

| 6,120,836 A | 9/2000 | Usuki |
|---|---|---|
| 8,536,322 B2 | 9/2013 | Han |

(Continued)

FOREIGN PATENT DOCUMENTS

| DE | 4307262 A1 * | 9/1994 |
|---|---|---|
| DE | 19912799 A * | 9/1999 |

(Continued)

OTHER PUBLICATIONS

Communication pursuant to Article 94(3) EPC issued Nov. 28, 2019 in corresponding European Patent Application No. 16 743 959.5, 4 pages.
Extended European Search Report and Written Opinion issued Jul. 26, 2018 in corresponding European Application No. 16743959.5.
(Continued)

*Primary Examiner* — Pranav N Patel
(74) *Attorney, Agent, or Firm* — MH2 Technology Law Group, LLP

(57) ABSTRACT

Disclosed herein is a novel method to fabricate magnetic silica nanomembranes using thin polymer cores based on silica deposition and self-wrinkling induced by thermal shrinkage. These micro- and nano-scale structures have vastly enlarged the specific area of silica, thus the magnetic silica nanomembranes can be used for solid phase extraction of nucleic acids. The magnetic silica nanomembranes are suitable for nucleic acid purification and isolation and demonstrated better performance than commercial particles in terms of nucleic acid recovery yield and integrity. In addition, the magnetic silica nanomembranes may have high nucleic acid capacity due to significantly enlarged specific surface area of silica. Methods of use and devices comprising the magnetic silica nanomembranes are also provided herein.

22 Claims, 13 Drawing Sheets

Related U.S. Application Data division of application No. 15/538,149, filed as application No. PCT/US2016/014920 on Jan. 26, 2016, now Pat. No. 10,737,276.

(51) Int. Cl.
| | | |
|---|---|---|
| *B03C 1/28* | (2006.01) | |
| *B03C 1/30* | (2006.01) | |
| *C01B 33/12* | (2006.01) | |
| *C08J 7/06* | (2006.01) | |
| *C12N 15/10* | (2006.01) | |
| *G01N 1/40* | (2006.01) | |
| *G01N 35/00* | (2006.01) | |

(52) U.S. Cl.
CPC .............. *B03C 1/288* (2013.01); *C01B 33/12* (2013.01); *C08J 7/06* (2013.01); *C12N 15/1013* (2013.01); *C12N 15/1017* (2013.01); *G01N 1/405* (2013.01); *G01N 35/0098* (2013.01); *G01N 35/0099* (2013.01); *B03C 2201/18* (2013.01); *B03C 2201/26* (2013.01); *C08J 2323/00* (2013.01)

(58) Field of Classification Search
CPC .......... B01D 15/424; C01B 33/12; C08J 7/06; C08J 2323/00; C12N 15/1013; C12N 15/1017; G01N 1/405; G01N 35/0098; G01N 35/0099

See application file for complete search history.

(56) References Cited

U.S. PATENT DOCUMENTS

| | | | |
|---|---|---|---|
| 2003/0040129 A1* | 2/2003 | Shah | ................ G01N 33/54326 |
| | | | 436/526 |
| 2005/0106602 A1 | 5/2005 | Akhavan-Tafti | |
| 2006/0177836 A1 | 8/2006 | McKernan et al. | |
| 2007/0087385 A1 | 4/2007 | Muller-Schulte | |
| 2009/0017518 A1 | 1/2009 | Wu et al. | |
| 2013/0164819 A1 | 6/2013 | Sjoblom et al. | |
| 2015/0037802 A1 | 2/2015 | Wang et al. | |

FOREIGN PATENT DOCUMENTS

| | | | |
|---|---|---|---|
| JP | H10247312 A | | 9/1998 |
| WO | WO8904373 | * | 5/1989 |
| WO | WO98/12717 A1 | | 3/1998 |
| WO | WO2009029859 | * | 3/2009 |
| WO | 2010/132610 A2 | | 11/2010 |

OTHER PUBLICATIONS

International Search Report and Written Opinion dated Jun. 30, 2016 from International Application No. PCT/US2016/014920, pp. 1-10.

Bogdanov et al., "Silicon Dioxide Thin Film Mediated Single Cell Nucleic Acid Isolation", PLoS One, Jul. 10, 2013, vol. 3, No. 7, Article No. e68280, 6 pages.

Zhang et al., "Spontaneous shrinking silica nanomembrane for solid phase DNA extraction", The 8th Annual IEEE International Conference on Nano/Micro Engineered and Molecular Systems, Apr. 7-10, 2013, Session 1E1-3, Article No. 243, p. 12.

* cited by examiner

HIERARCHICAL SILICA LAMELLA FOR MAGNETIC NUCLEIC ACID EXTRACTIONS

CROSS-REFERENCE TO RELATED APPLICATIONS

This application is a continuation application of U.S. patent application Ser. No. 16/917,751, filed 30 Jun. 2020, which is a divisional application of U.S. patent application Ser. No. 15/538,149, filed 20 Jun. 2017 (now U.S. Pat. No. 10,737,276), which is a U.S. National Stage Application of PCT/US2016/0149201, filed 26 Jan. 2016, which claims priority to U.S. Provisional Application No. 62/108,288, filed 27 Jan. 2015, the entire disclosures of which are hereby incorporated by reference in their entireties.

GOVERNMENT SUPPORT

This invention was made with government support under contract number R43GM109618 awarded by the National Institutes of Health. The government has certain rights in the invention.

BACKGROUND

Isolation of nucleic acids from samples such as cells, tissues, plants, bacteria, viral particles, blood, serum, or plasma may be an important step for genetic analysis. Conventionally, liquid phase extraction techniques, such as phenol/chloroform precipitation, are widely used. Although these approaches may yield nucleic acids of high quality, they can be laborious, time-consuming, and highly operator-dependent. Solid phase extraction techniques are a popular alternative. They are often the methods of choice when processing large numbers of samples. Commonly used solid-phase substrates include, for example, silica spin columns and silica magnetic particles that may provide large surface areas for nucleic acid binding. These porous matrices and micro/nano particles, however, may induce nucleic acid shearing as a result of flow and particle mixing, leading to decreased nucleic acid integrity.

The dominant methods of nucleic acid extraction, such as DNA extraction, have remained remarkably unchanged since spin columns and magnetic microparticles were first introduced. While methods such as spin columns and magnetic microparticles are fast and easy, the shear forces imposed by these methods may fragment the nucleic acids and may be incapable of sufficient nucleic acid quality for the new generation of long read length sequencing and genome mapping technologies. As such, there exists an unmet need to develop novel separation materials and methods that allow for easier isolation and purification of nucleic acids from biological samples.

Thermoplastic substrates have previously been disclosed that contain a hierarchical structure of microscale folds layered with nanoscale silica lamella that are easily fabricated using an inexpensive heat-shrinkable polyolefin (PO) film. This nanomembrane can be fine-tuned to create a non-porous, high surface area binding substrate capable of capturing vast amounts of nucleic acids without imparting nucleic acid fragmenting shear forces. By minimizing fragmentation, it may be possible to bias nucleic acid binding away from a prone conformation towards a tentacle conformation, increasing binding capacity to, for example, about 100 to about 1,000,000 times greater than previously reported for silica microparticles. Furthermore, the silica nanomembranes use a simple bind, wash, and elute protocol that combines the ease of column and bead extraction with the performance of phenol-chloroform, resulting in nucleic acid yields that can be about 10 times greater than either columns or magnetic beads and nucleic acids of high purity and high molecular weight.

To facilitate extraction of large amounts of high quality, high molecular weight nucleic acids from cells, tissues, and body fluids, disclosed herein is a magnetic silica nanomembrane material made by depositing a magnetic component on or embedded in a thermoplastic substrate in addition to at least one silica layer. The magnetic silica nanomembrane enables extraction to proceed analogously to a magnetic process whereby a magnet can be used to draw the nanomembrane to a side or bottom of a container, such as a test tube, thereby facilitating pipetting and washing without disturbing the nanomembrane or the bound nucleic acids.

Disclosed herein are inexpensive magnetic thermoplastic nanomembrane materials that use a hierarchical layering of micro- and nanoscale silica lamella and a magnetized layer to create a high surface area and low shear substrate capable of capturing vast amounts of high molecular weight nucleic acid without fragmentation.

BRIEF SUMMARY

Disclosed herein are magnetic silica nanomembranes comprising a polymer core having a first surface and a second surface; at least one silicon dioxide layer disposed over the polymer core, the silicon dioxide layer comprising at least one surface morphology chosen from a plurality of (a) microscale silica structures and (b) nanoscale silica structures; and at least one magnetic component.

In certain embodiments, the at least one magnetic component comprises at least one magnetic material chosen from diamagnetic materials, paramagnetic materials, ferrimagnetic materials, and ferromagnetic materials, and in certain embodiments, the at least one magnetic component comprises at least one magnetic material chosen from iron, nickel, cobalt, magnetite, hematite, maghemite, and alloys of magnetic materials such as steel, alperm, permalloy, femico, sendust, cunife, and alnico.

In certain embodiments, the at least one magnetic component is chosen from at least one layer of magnetic material disposed over the polymer core, at least one magnetic material embedded within the polymer core, and at least one polymer core being magnetic. In certain exemplary embodiments, the at least one magnetic component is a magnetic layer having a thickness ranging from about 5 nm to about 10 μm thick.

In certain embodiments, the at least one magnetic component comprises a layer of magnetic material disposed over the at least one silicon dioxide layer. In certain embodiments disclosed herein, the at least one silicon dioxide layer is disposed over the first surface of the polymer core and the at least one magnetic component is a magnetic layer disposed over the second surface. In certain embodiments, a first silicon dioxide layer is disposed over the first surface of the polymer core, the at least one magnetic component is a magnetic layer disposed over the second surface, and a second silicon dioxide layer is disposed over the at least one magnetic component. In various other exemplary embodiments, a first silicon dioxide layer is disposed over the first surface of the polymer core, the at least one magnetic component is a magnetic layer disposed over the second surface, a second silicon dioxide layer is disposed over the at least one magnetic component, and a third silicon dioxide layer is disposed between the first surface of the polymer core and the at least one magnetic component. In further embodiments, a first silicon dioxide layer is disposed over a first surface of the polymer core, at least one magnetic component is disposed over a second surface of the polymer core, a second silicon dioxide layer is disposed over the at least one magnetic component, a third silicon dioxide layer is disposed between the second surface of the polymer core and the at least one magnetic component, a second magnetic component is disposed over the first silicon dioxide layer disposed over the first surface of the polymer core, and a fourth silicon dioxide layer is disposed over the second magnetic component. In various embodiments, a second magnetic component is disposed between the first surface of the polymer core and the at least one silicon dioxide layer. In certain embodiments, the magnetic nanomembrane disclosed herein further comprises a passivation layer disposed over the at least one magnetic component, and in certain embodiments, the at least one silicon dioxide layer has a thickness ranging from about 2 nm to about 500 nm thick.

In certain embodiments disclosed herein, the at least one silicon dioxide layer is deposited using a deposition method chosen from electron beam evaporation, sputtering, chemical vapor deposition, plasma enhanced chemical vapor deposition, electroplating, atomic layer deposition, chemical solution deposition, and spin coating. In various other embodiments disclosed herein, the magnetic silica nanomembranes disclosed herein further comprise a surface functionalization chosen from at least one of aminopropyl groups, chloropropyl groups, octadecyl groups, octyl groups, quaternary ammonium groups, diethlylaminoethyl group, sulfonic acid groups, phenyl groups, chitosan, biotin, streptavidin, antibodies, proteins, lipids, polyethylene glycol, and enzymes. In certain exemplary embodiments, the polymer core of the magnetic silica nanomembranes disclosed herein comprises at least one thermoplastic material chosen from polymethyl methacrylate, polycarbonate, polystyrene, cyclic polyolefin polymers, polypropylene, polyvinyl chloride, polyethylene, fluorinated ethylene propylene, polytetrafluoroethylene, and polyvinylidene fluoride.

Also disclosed herein are methods for extracting nucleic acids from a sample, the methods comprising obtaining a sample comprising nucleic acids; contacting the sample with at least one magnetic nanomembrane, the at least one magnetic nanomembrane comprising at least one silicon dioxide layer and at least one magnetic component; allowing the nucleic acids in the sample to adsorb onto the at least one magnetic nanomembrane; manipulating the at least one magnetic nanomembrane using a magnet; and desorbing the nucleic acids from the at least one magnetic silica nanomembrane to obtain extracted nucleic acids from the sample.

In certain embodiments of the methods disclosed herein for extracting nucleic acids from a sample, the nucleic acids are chosen from DNA, RNA, and mixtures of DNA and RNA. In certain embodiments, the nucleic acids are dispersed in a supernatant comprising a lysis buffer, or, in certain embodiments, the nucleic acids are dispersed in a reaction solution.

In certain embodiments of the methods disclosed herein, manipulating the at least one magnetic nanomembrane comprises holding the magnetic nanomembrane in a desired position with the magnet while removing the solution from contact with magnetic nanomembrane, and magnetically releasing, and in certain embodiments, manipulating the at least one magnetic nanomembrane comprises transferring the magnetic nanomembrane with the magnet and magnetically releasing the at least one magnetic nanomembrane after transfer.

In certain embodiments of the methods disclosed herein, washing the at least one magnetic nanomembrane comprises a) contacting the at least one magnetic nanomembrane with a wash solution; and b) manipulating the at least one magnetic nanomembrane to separate the wash solution from the magnetic nanomembrane. In various embodiments, the methods disclosed herein may further comprise repeating the process of steps a) and b) one or more times.

In certain embodiments of the methods disclosed herein, desorbing the nucleic acids comprises contacting the sample with an elution solution and releasing the at least one magnetic nanomembrane into the elution solution, and in certain embodiments, the extracted nucleic acids have an average length of at least about 100 kilobases. Also disclosed herein are embodiments wherein the method for extracting nucleic acids from a sample is performed in an automated manner by a robotic instrument.

Further areas of applicability of the embodiments disclosed herein will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
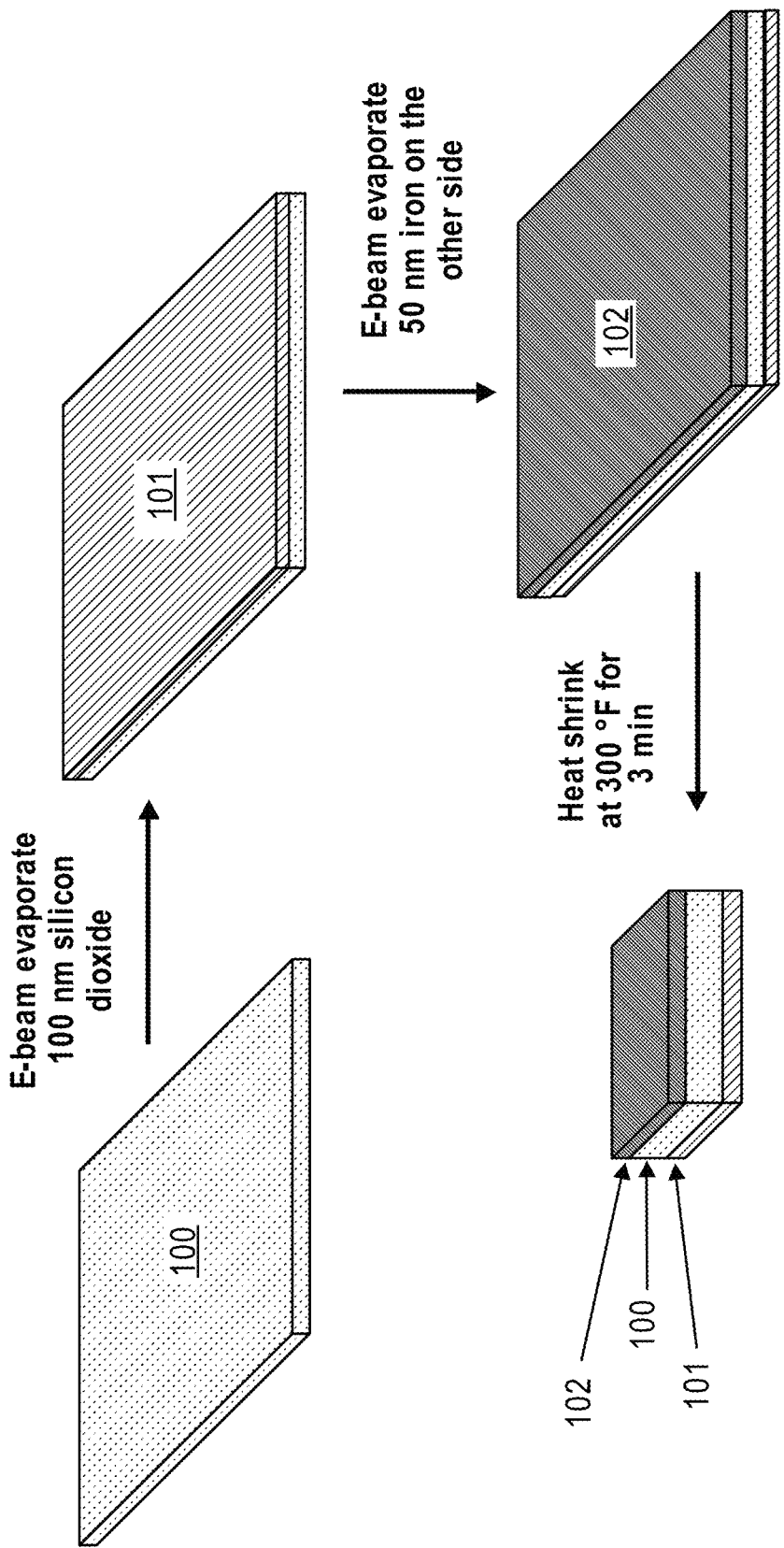
FIG. 1 is a diagram illustrating a fabrication process for a magnetic silica nanomembrane comprising a polymer core, a layer of silicon dioxide, and a layer of iron.

The following description of various embodiments is merely exemplary in nature and is in no way intended to limit the disclosure, its applications, or uses thereof.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "one or more of" with respect to a listing of items such as, for example, A and B, means A alone, B alone, or A and B. The term "at least one of" is used to mean one or more of the listed items can be selected.

Unless otherwise specified, all percentages and amounts expressed herein and elsewhere in the specification should be understood to refer to percentages by weight. The amounts given are based on the active weight of the material.

Disclosed herein are nucleic acid extraction methods based on novel and relatively inexpensive hierarchical magnetic silica nanomembranes. The magnetic silica nanomembranes disclosed herein are polymer substrates containing a hierarchical topography of microscale and/or nanoscale silica structures and at least one magnetic component. As used herein, a microscale structure is understood as having characteristic dimensions of less than or about 1000 µm, such as less than or about 500 µm, less than or about 200 µm, or less than or about 100 µm. As used herein, a nanoscale structure is understood as having characteristic dimensions of less than or about 1000 nm, such as less than or about 500 nm, less than or about 200 nm, or less than or about 100 nm. Unlike silica magnetic beads and columns, which impart DNA/RNA fragmenting shear forces, the non-porous silica nanomembrane substrates disclosed herein can bind and release DNA/RNA without fragmenting it, achieving increased DNA/RNA size (up to the Mb range), which may exceed phenol-chloroform extractions, considered by many to be a gold standard in the art. Moreover, the methods disclosed herein for nucleic acid extraction using magnetic silica nanomembranes may in many respects be simpler than magnetic beads and columns. Furthermore, the methods disclosed herein may have an extraction yield that is at least about five to about thirty fold greater than known methods employing magnetic beads and/or columns.

The magnetic silica nanomembranes disclosed herein may be used to extract nucleic acids from cultured cells, tissues, bacteria, virus, plant cells, whole blood, serum, buffy coat, plasma, urine, sputum, stool, pleural effusion, cerebral spinal fluid, ductal lavage, formalin-fixed paraffin embedded (FFPE) tissue samples, or other nucleic acid containing materials. It is understood to one skilled in the art that modifications to the extraction buffer systems may be necessary to accommodate different sample types.

As used herein, the term "silica nanomembranes" means three-dimensional conformations of the silica on a polymer core, which can comprise structures such as micro-wrinkles, nano-wrinkles and silica flakes, ranging from tens of nanometers to micrometers in size. The terms lamella, wrinkle, fold, flake, chip, and the like are descriptive terms used to describe the appearance of silica structures on the nanomembrane surface. As one of ordinary skill in the art would appreciate, the topography adopted by the silica at the microscale and/or nanoscale level may vary according to various factors, including, for example, the amount of silicon dioxide deposited and the unique conformation adopted by the polymer core during shrinkage, and the embodiments disclosed herein are not limited by the topography adopted by the at least one silicon dioxide layer that is deposited over the polymer core.

The term "silica" as used herein means silicon oxide, silicon dioxide and silicon dioxide derivatives, such as $SiO_2$ crystals and other forms of $SiO_2$, for example diatoms composed of $SiO_2$, zeolites, amorphous silicon dioxide, glass powder, silicic acid, waterglass, borosilicate, and also aluminum silicates and activated silicates.

The term "sample" or "biological sample" as used herein refers to any sample that comprises cells or cellular material, such as cells, frozen cell pellets, fixed cells, feces/stool, buffy coat (i.e., white blood cell fraction of blood), ascites, swabs, such as cheek or throat swabs, cervical swabs, sputum, organ punctates, sperm, tissue samples, fixed tissue samples, tissue sections of fixed or nonfixed tissue samples, such as frozen sections and paraffin sections, such as formalin-fixed paraffin sections, tumor material, biopsy samples, blood samples, such as whole blood or blood fractions, cell suspensions, and in the broadest sense all samples that comprise cellular constituents, wherein both intact cells and cell constituents shall be comprised. Furthermore, the term also comprises other nucleic acid-containing, biological materials, such as, for example, blood serum or blood plasma, such as virus-containing serum or plasma, HIV- and HCV-infected serum samples, secretions, CSF, bile, lymph fluid, and urine. Similarly, it can be nucleic acid-containing materials that originate from biochemical or biotechnological processes and are to be subsequently purified.

As used herein, the term "nucleic acid" includes "polynucleotide," "oligonucleotide," and "nucleic acid molecule," and generally means a polymer of DNA or RNA, which can be single-stranded or double stranded, synthesized or obtained (e.g., isolated and/or purified) from natural sources, which can contain natural, non-natural or altered nucleotides, and which can contain a natural, non-natural or altered internucleotide linkage, such as a phosphoramidate linkage or a phosphorothioate linkage, instead of the phosphodiester found between the nucleotides of an unmodified oligonucleotide. In certain embodiments the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In certain embodiments, the nucleic acids disclosed herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

As used herein, the term "polymer" means any polymer substrate that is capable of heat shrinkage. In some embodiments, the polymers are thermoplastic polymers. As used herein, the term "thermoplastic" means a polymer that becomes pliable or moldable above a specific temperature and returns to a solid state upon cooling. Thermoplastics can include, for example, polymers such as polymethyl methacrylate (PMMA), polycarbonate, polystyrene (PS), and cyclic polyolefin (PO) polymers.

The silica nanomembranes used herein may be manufactured using commonly used polymer substrates, including, for example, pre-stretched thermoplastics, such as PMMA, polycarbonate, PS, and cyclic PO polymers. Other exemplary polymer substrates that may be used as the polymer core of the silica nanomembrane include, for example, polyvinyl chloride, polyethylene, polypropylene, fluorinated ethylene propylene, polytetrafluoroethylene, and polyvinylidene fluoride. In certain embodiments, silica may be deposited over shrinkable PO films. After incubation at elevated temperatures, the polymer film shrinks, and the silica forms nanostructures due to the aforementioned mechanism.

In certain embodiments, the polymer core of the magnetic silica nanomembrane has a shrunken thickness ranging from about 5 µm to about 5 mm. In certain embodiments, the polymer core of the magnetic silica nanomembrane has a pre-shrunken thickness ranging from about 5 µm to about 500 mm.

In certain embodiments disclosed herein, the magnetic silica nanomembrane may be fabricated by coating the polymer core, such as a polyolefin polymer film, with at least one layer of silicon dioxide. In certain embodiments, the at least one layer of silicone dioxide may range in thickness from about 2 nm to about 500 nm, such as about 50 nm to about 200 nm, about 75 nm to about 150 nm, or about 100 nm. In one embodiment, a 20 µm thick polyolefin film is coated on one side with a 100 nm thick layer of silicon dioxide using e-beam evaporation. The silicon dioxide may be deposited directly on the polymer core, or, alternatively, in certain embodiments the silicon dioxide may be deposited over the polymer core when the polymer core is first coated with at least one magnetic component, at least one inert layer, and/or at least one additional layer of silicon dioxide.

After the polymer core has been coated with at least one layer of silica, the other side of the polymer core may then be coated with at least one magnetic component, or, in certain embodiments, a second layer of silica. In certain embodiments, the other side of the silica-coated polymer core is then coated with at least one magnetic component, and in certain embodiments the other side of the silica-coated polymer core is first coated with a second silica layer, wherein the second silica layer is then coated with at least one magnetic component.

In certain embodiments disclosed herein, the other side of the polymer core, such as the polyolefin film, may then coated with a magnetic component. In certain embodiments, the magnetic component may be a magnetic layer ranging in thickness from about 15 nm to about 200 nm, such as about 30 nm to about 100 nm, about 100 nm or about 30 nm thick. In certain embodiments, the magnetic component may be embedded within the polymer core. In certain embodiments, the polymer core may be comprised of a material that is intrinsically magnetic.

In certain embodiments, a polymer core, such as a polyolefin film ranging in thickness from about 10 µm to about 100 µm, may be coated on one side with a layer of silicon dioxide. The other side of the polymer core may then be coated with a magnetic layer, such as a 20 nm to 100 nm thick magnetic layer. The coated polymer core substrate may then be heat shrunk, for example in an oven. This creates a nanomembrane with micro- and nanoscale silica structures on one side and a magnetic layer on the other side that can then be used for magnetic nucleic acid extraction. In certain embodiments, the magnetic layer may also have nanoscale and microscale structures created by the created during the fabrication process. FIG. 1 is a flow chart illustrating an exemplary fabrication process according to embodiments disclosed herein. As shown in FIG. 1, at least one silicon dioxide layer 101 may be deposited over a first surface of a polymer core 100, such as a polyolefin film. Next, at least one magnetic component 102, such as iron, may be deposited over a second surface of the polymer core 100 before the nanomembrane is heat shrunk.

Figure 2:
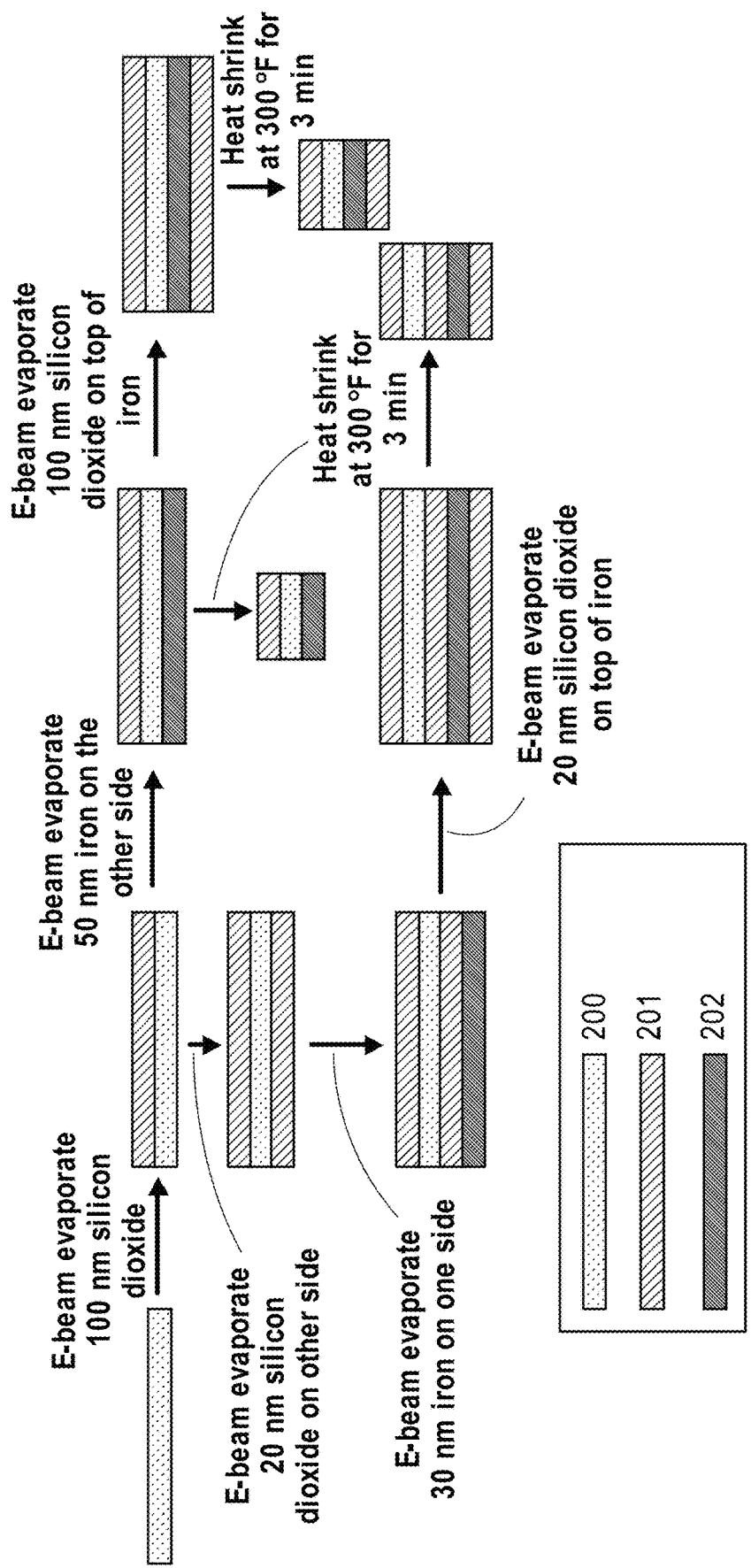
FIG. 2 illustrates a fabrication process for a magnetic silica nanomembrane comprising a polymer core, multiple layers of silicon dioxide, and a layer of iron.

In certain embodiments, the nanomembrane coated with silicon dioxide on one side may be alternately coated with iron and silicon dioxide on the other side, and then the coated polyolefin substrate may be heat shrunk. This creates a nanomembrane with micro- and nanoscale silica structures on both sides. The back side silica structures comprise a ferromagnetic iron layer covered by silica such that magnetic manipulation can be performed and nucleic acids can bind to both sides of the nanomembrane. The silica covering the iron acts as a binding surface for nucleic acids and protects the iron from reacting with buffer components. FIG. 2 is a flow chart illustrating various exemplary fabrication processes according to embodiments disclosed herein. As shown in FIG. 2, at least one silicon dioxide layer 201 may be deposited over a first surface of a polymer core 200, such as a polyolefin film. Next, at least one magnetic component 202, such as iron, may be deposited over a second surface of the polymer core 200. In certain embodiments, a second silicon dioxide layer 201 may be deposited over the at least one magnetic component 202 before the nanomembrane is heat shrunk.

Alternatively, as shown in FIG. 2, at least one silicon dioxide layer 201 may be deposited over a first surface of the polymer core 200, and a second silicone dioxide layer 201 may be deposited over a second surface of the polymer core 200. Next, at least one magnetic component 202, such as iron, may be deposited over the second silicon dioxide layer 201. Finally, a third silicon dioxide layer 201 may be deposited over the at least one magnetic component 202 before the nanomembrane is heat shrunk.

In certain embodiments of the disclosure, a first silicon dioxide layer may be deposited on a first surface of the polymer core, and at least one magnetic component may be deposited on the second surface of the polymer core, wherein a second silicon dioxide layer may be deposited over the at least one magnetic component. Furthermore, in certain embodiments, a second magnetic component may be deposited between the first silicon dioxide layer and the first surface of the polymer core.

Figure 14A:
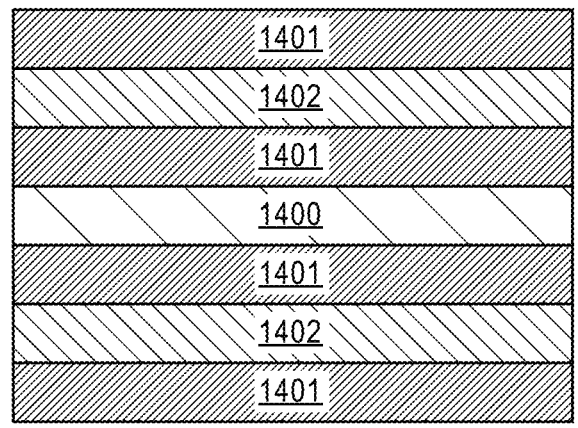
FIGS. 14A, 14B, and 14C illustrate various exemplary embodiments of magnetic silica nanomembranes comprising a polymer core, at least one layer of silicon dioxide, and at least one magnetic component.

As shown in FIG. 14A, in certain embodiments, at least one layer of silicon dioxide 1401 may be deposited over a first surface of the polymer core 1400 and at least one magnetic component 1402 may be deposited over the at least one silicon dioxide layer 1401. In certain embodiments, a second silicon dioxide layer 1401 may be deposited over the at least one magnetic component 1402. Optionally, no layers may be deposited on a second surface of the polymer core 1400, such that, for example, the nanomembrane contains a polymer core 1400, a first layer of silicon dioxide 1401, a magnetic component 1402, and a second layer of silicon dioxide 1401.

Alternatively, in certain embodiments and as shown in FIG. 14A, at least one layer of silicon dioxide 1401 may be deposited over a first surface of the polymer core 1400 and at least one second layer of silicon dioxide 1401 may be deposited over a second surface of the polymer core 1400. Next, at least one magnetic component 1402 may be deposited over the at least one silicon dioxide layer 1401 and a second magnetic component 1402 may deposited over the second silicon dioxide layer 1401. Finally, in various optional embodiments illustrated in FIG. 14A, a third layer of silicon dioxide 1401 may be deposited over the at least one magnetic component 1402, and, optionally, a fourth layer of silicon dioxide 1401 may be deposited over the second magnetic component 1402.

Figure 14B:
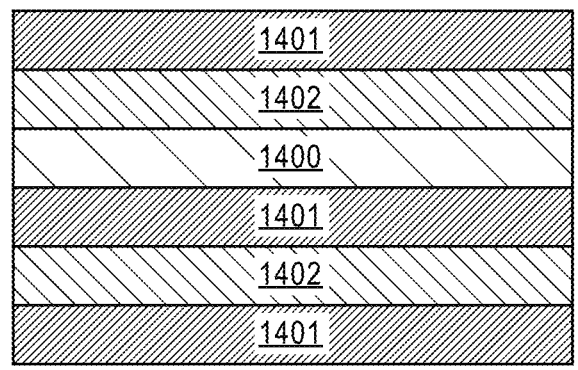

As shown in FIG. 14B, in certain embodiments, at least one magnetic component 1402 may be deposited over a first surface of a polymer core 1400, and at least one layer of silicon dioxide 1401 may be deposited over the at least one magnetic component. In various optional embodiments, no layers may be deposited on a second surface of the polymer core 1400, such that, for example, the nanomembrane contains a polymer core 1400, a magnetic component 1402, and a silicon dioxide layer 1401.

In certain other embodiments illustrated in FIG. 14B, at least one first magnetic component 1402 may be deposited over a first surface of a polymer core 1400 and at least one layer of silicon dioxide 1401 may be deposited over a second surface of the polymer core 1400. Next, a second magnetic component 1402 may be deposited over the at least one layer of silicon dioxide 1401. Optionally, in certain embodiments, a second layer of silicon dioxide 1401 may be deposited over the second magnetic component 1402. In certain other embodiments illustrated in FIG. 14B, a third layer of silicon dioxide 1401 may be deposited over the at least one first magnetic component 1402.

Figure 14C:
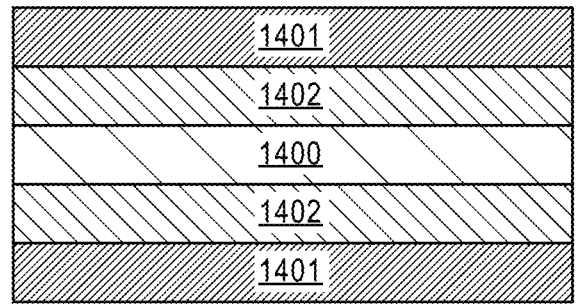

As shown in FIG. 14C, in certain embodiments, at least one first magnetic component 1402 may be deposited on a first surface of a polymer core 1400 and at least one second magnetic component 1402 may be deposited on a second surface of the polymer core 1400. The magnetic components may be the same or different. In certain embodiments, at least one layer of silicon dioxide 1401 may be deposited over the at least one first magnetic component 1402. In certain exemplary embodiments, optionally a second layer of silicon dioxide 1401 may be deposited over the second magnetic component 1402.

In various other embodiments, a polyolefin film may be coated on one side with a silicon dioxide and then heat shrunk. Next, a magnetic layer may be deposited on the other side of the nanomembrane after heat shrinking. In alternate embodiments disclosed herein, after the polyolefin film is heat shrunk, the at least one magnetic component may be coated with silicon dioxide to act as a passivation layer.

In certain embodiments disclosed herein, the magnetic component can be diamagnetic, paramagnetic, ferromagnetic, or ferrimagnetic. In various embodiments, the magnetic component is paramagnetic such that the nanomembranes do not stick to one another. In various embodiments, the magnetic component can be made from iron, nickel, cobalt, magnetite, hematite, maghemite, magnetic alloys such as steel, permalloy, and alnico, or any such material.

In certain exemplary embodiments, the magnetic material may have a high magnetic susceptibility such that a thinner layer of the magnetic material can be deposited while achieving sufficient magnetic force to pull the nanomembrane while in solution. A thicker layer may result in a larger magnetic pulling force for a given applied magnetic field. For efficient magnetic manipulation, sufficient magnetic force is necessary to overcome viscous forces, surface tension, buoyancy, and the like. In one embodiment, the magnetic layer can vary in thickness from about 2 nm to about 10 μm.

In certain embodiments the magnetic material may be chemically and biologically inert such that it does not degrade, leech, or adversely react with buffer components or biological materials. The magnetic material may also not be highly stressed and not disrupt the formation of the silica lamella structures that are necessary for nucleic acid extraction.

After deposition, the coated polymer core is then heat shrunk in an oven. This creates a nanomembrane with micro- and nanoscale silica structures, such as lamella, on one side and a magnetic layer on the other side, which can then be used for magnetic nucleic acid extraction.

As the polymer film shrinks, differences in film stress create a hierarchical structure of microscale folds layered with nanoscale silica lamella that can be fine tuned via silicon dioxide deposition thickness.

In various embodiments disclosed herein, the polymer core may be coated on one side with a first layer of silicon dioxide. The other side of the polyolefin film may then alternately coated with a second layer of silicon dioxide, followed by a layer of a magnetic material on top of the second layer of silicon dioxide, and a third layer of silicon dioxide on top of the layer of the magnetic material. The coated polymer substrate may then be heat shrunk, for example in an oven. In certain embodiments the coated polymer substrate may be heat shrunk. Ibis creates a nanomembrane with micro- and nanoscale silica lamella on both sides. The backside silica lamella comprises a magnetic center sandwiched by silica such that magnetic manipulation can be performed and nucleic acids can bind or adsorb to both sides of the nanomembrane. The silica enveloping both sides of the magnetic material acts as a binding surface for nucleic acids and protects the magnetic material from reacting with buffer components. In certain embodiments, the magnetic material may be iron. In other embodiments, the magnetic material may be an alloy such as steel, alnico, permalloy, alperm, femico, sendust, cunife, or the like.

In another embodiment, the polymer core may be coated on one side with a first silica layer. The other side of the polymer film may then be alternately coated with a layer of a magnetic material and a second silica layer. The coated polymer substrate may then be heat shrunk.

In another embodiment, a polymer core may be coated on one side with a silica layer and then heat shrunk. Next, a magnetic layer may be deposited on the other side of the nanomembrane after heat shrinking.

In the embodiments disclosed herein, the deposition of the layers may be done by any means known in the art. In certain embodiments, the layers can be deposited by thermal evaporation, electron beam evaporation, sputtering, chemical vapor deposition, plasma enhanced chemical vapor deposition, electroplating, atomic layer deposition, chemical solution deposition, spin coating, or any other deposition method. In one embodiment, the layers can be deposited by electron beam evaporation.

In other embodiments, the magnetic layer may be passivated by depositing another layer or coating to make it more chemically or biologically inert.

In certain embodiments disclosed herein, the silica comprising the silica nanomembranes may be derivatized or functionalized with other compounds or components known in the art to provide desirable chemical, physical, or electronic properties or to perform specific functions such as to promote or prevent adsorption or binding and facilitate biochemical reactions. In some embodiments, the silica can be derivatized with aminopropyl groups, chloropropyl groups, octadecyl groups, octyl groups, quaternary ammonium groups, diethlylaminoethyl group, sulfonic acid groups, phenyl groups, biotin, streptavidin, antibodies, proteins, lipids, chitosan, or enzymes.

In various embodiments, the magnetic component may be covered by a silica layer to enable nucleic acid binding on both sides of the nanomembrane.

In some embodiments, the nanomembrane is heated at a temperature ranging from about 100° F. to 500° F., such as about 200° F. to about 400° F., or about 250° F. to about 300° F. In some embodiments the nanomembrane is heated for a time ranging from about 10 seconds to about 10 minutes, such as about 1 minute to about 5 minutes, or about 2 minutes to about 3 minutes. In some embodiments, stress may be applied to the nanomembrane to control the shrink rate and direction.

In one embodiment, the nanomembrane may be shaped to specific dimensions after heat shrinking by cutting or punching. In certain embodiments, for example, a disk of the nanomembrane may formed using a punch after heat shrinking, such as a disk ranging is diameter from about 1 μm to several meters, such as about 1 mm to about 6 mm. In another embodiment, the nanomembrane may be shaped to specific dimensions before heat shrinking by cutting or punching.

The hierarchical pattern on the silica nanomembranes disclosed herein is based on the thermally induced surface wrinkling of heat-shrinkable polymer film deposited with silica. The use of surface wrinkles caused by shrinking or swelling with a pre-stretched soft polymer substrate coated thin film of metals is a simple and low-cost method to fabricate nanomaterials. Due to different shrinkage or expansion coefficients between the polymer substrate and the stiff film, stress will accumulate within the film and eventually lead to spontaneous surface wrinkling.

The exact nanostructures formed in the process of making the magnetic silica nanomembranes depends on the thickness of the coating or layer of silicon dioxide and the magnetic material being deposited. As the silica layer gets thicker, the specific surface area of the silica nanomembrane may be greatly enhanced, and, concomitantly, the nucleic acid binding capacity increases. Thus, the magnetic silica nanomembranes disclosed herein may have higher nucleic acid recovery yield compared to commercial silica columns and magnetic particles. The magnetic silica nanomembranes disclosed herein may be able to extract nucleic acid, such as DNA, from cultured human cells with high yield and high quality compared to other known methods, such as the phenol-chloroform method.

The magnetic silica nanomembranes disclosed herein can be fabricated into any suitable shape for specific purposes, such as planar or in a bead conformation. In certain embodiments, the magnetic silica nanomembranes can be circular, square, or any particular shape, including irregular, novelty, and three-dimensional shapes. In one embodiment, the magnetic silica nanomembranes disclosed herein can be circular and can fit into a test tube. In certain embodiments, the magnetic silica nanomembranes can be adapted to fit into a column or pipette tip for flow-through analysis or any other apparatus capable of holding a sample. In certain embodiments, the magnetic silica nanomembranes can be folded, bent, or attached together into a three-dimensional shape.

In certain embodiments, disclosed herein is a method for making a magnetic silica nanomembrane comprising: a) depositing onto a polymer core having an original size, at least one layer of silicon dioxide; b) depositing onto the polymer core at least one magnetic component; and c) heating the polymer core at a sufficient temperature and time to allow the polymer core to shrink, and wherein the shrinking of the polymer core creates silica microstructures and/or nanostructures on the surface of the silica nanomembrane. In certain embodiments, a method of making a magnetic silica nanomembrane is disclosed herein comprising: a) depositing onto a first side of a polymer core having an original size, at least one layer of silicon dioxide; b) depositing onto a second side of the polymer core at least one magnetic layer; and c) heating the polymer core at a sufficient temperature and time to allow the polymer core to shrink, and wherein the shrinking of the polymer core creates silica microstructures and/or nanostructures on the surface of the silica nanomembrane.

The magnetic silica nanomembranes disclosed herein may be fabricated using simple, inexpensive, and/or inventive thermoplastic processes. In some embodiments, a range of about 2 nm to about 500 nm of silicon dioxide is deposited onto about 5 μm to about 500 μm thick polymer core, such as a polyolefin film, by any known means of deposition. Examples of deposition methods may include, but are not limited to chemical vapor deposition, electrophoretic deposition, dip-coating, physical vapor deposition, electron beam vapor deposition, sputtering, spin-coating, or liquid phase deposition.

The silica coated polymer film is then heat shrunk in an oven at a temperature sufficient to shrink the polymer. The temperature can vary as a function of the type of polymer used and the starting thickness of the polymer. Any heating means can be used, such as, for example, infrared heater, heat gun, or resistive heating element. In certain embodiments, the polymer is heated in a temperature range of between about 100° F. to about 500° F., such as about 250° F. or about 300° F.

The heating time for the shrinking process can also vary as a function of the type of polymer used and the starting thickness of the polymer. In some embodiments, the polymer may be heated for between about 10 seconds to about 10 minutes, such as about 2 to about 3 minutes.

The heat shrinking of the polymer may cause the film to shrink in area by over 95% in size, while increasing in thickness, and creates a hierarchical structure of microscale folds topped by nanoscale flakes. The magnetic silica nanomembranes can then be fabricated into a variety of shapes or sizes as needed for various applications. In some embodiments, the polymer core film may shrink to between about 0.1% to about 95% or about 75% of its original size when subjected to heat shrinking. It is envisioned that the methods disclosed herein may be practiced on any scale, including small-scale batch processes and industrial scale roll-to-roll processes.

In certain embodiments, the magnetic silica nanomembranes may be punched into circles of varying diameter. In one embodiment, 6 mm diameter pieces can be used, which are capable of fitting into a common 1.5 mL tube. In certain embodiments, 1 mm diameter or smaller pieces can be used, to reduce wetting volume and fluidic dead volume to facilitate extraction of microvolume and low abundance samples. In certain embodiments, the magnetic silica nanomembranes disclosed herein may be capable of binding more than about 150 μg of DNA each, such as more than about 160 μg of DNA each, or about 175 μg or more of DNA each. In certain embodiments, the magnetic silica nanomembranes disclosed herein may be capable of binding more than about 250 μg of total nucleic acid each, such as more than about 500 μg of total nucleic acid each, or about 1000 μg or more of total nucleic acid each. In certain embodiments disclosed herein, the magnetic silica nanomembranes may remain stable for more than at least about six months. In one embodiment, a 6 mm circle of silica nanomembranes can fit into a cap of a 1.5 mL tube and be used for nucleic acid separations. These tubes can be premade and available as a kit, which may include instructions for use, for example, along with reagents for sample preparation and clean up.

Figure 3:
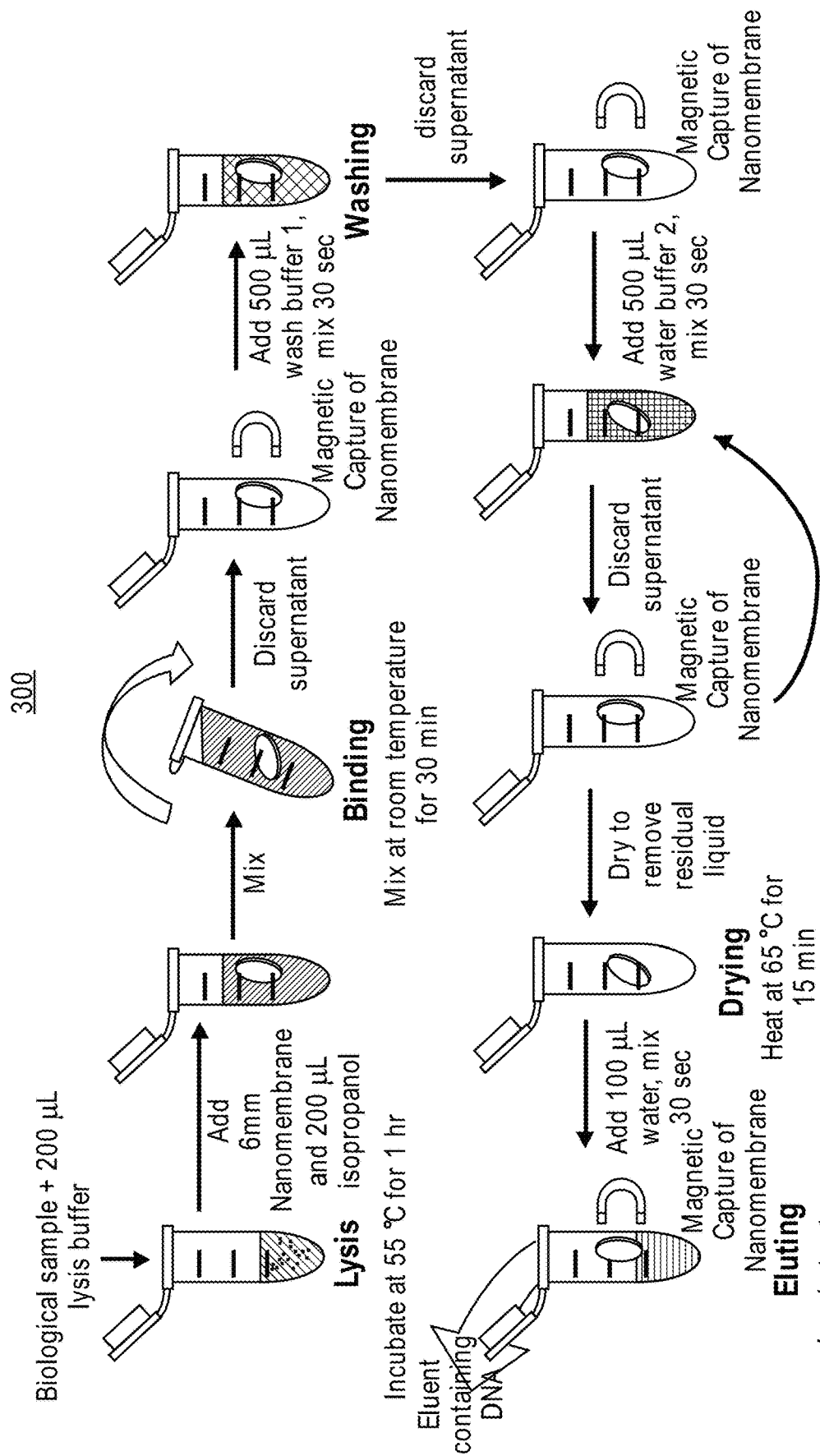
FIG. 3 is a flow chart illustrating an exemplary method for DNA extraction using a magnetic silica nanomembrane.

In accordance with certain embodiments, disclosed herein is a method for extracting nucleic acids from a sample comprising: a) obtaining a sample comprising nucleic acids; b) contacting the sample with a sufficient amount of magnetic silica nanomembrane; c) allowing the nucleic acids in the sample to adsorb onto the magnetic silica nanomembrane; d) moving the magnetic silica nanomembrane using a magnet; e) optionally washing the magnetic silica nanomembrane to remove any non-nucleic acid components; and f) desorbing the nucleic acids from the magnetic silica nanomembrane to obtain the isolated and purified nucleic acids from the sample. An exemplary method 300 for the extraction of nucleic acids from a sample are illustrated schematically in the flow chart shown in FIG. 3.

In some embodiments, the method for extracting the nucleic acids using the magnetic silica nanomembranes disclosed herein may include at step a) contacting the nucleic acids with a chaotropic agent. This may help the nucleic acids to adsorb or bind to the silica microstructures and nanostructures on the nanomembrane. Chaotropic agents or compounds are compounds that change or disrupt the secondary structure, tertiary structure, and quaternary structure of proteins, nucleic acids, and protein-nucleic acid complexes while the primary structure remains intact. In solution, under chaotropic conditions, the intramolecular interactions of biological molecules, such as proteins, protein-nucleic acid complexes, and nucleic acids, are disrupted, since chaotropic compounds interfere with stabilizing intramolecular interactions in biological molecules, for example hydrogen bonds, van der Waals forces, and hydrophobic effects. Chaotropic compounds usually have large-volume ions that, owing to their size, can interfere with the intermolecular interactions and reduce the polarity of the solvent as a result, thereby disrupting intermolecular and intramolecular hydrogen bonds. Consequently, many proteins precipitate; however, the helical structure of double-stranded nucleic acid segments is maintained. By adding chaotropic compounds to cell lysates or cell suspensions, proteins can be precipitated while nucleic acids remain in solution. Under chaotropic conditions, the binding of nucleic acids to silicon dioxide-based matrices is greatly favored. Chaotropic compounds comprise, for example, high concentration urea solutions (e.g., 6 to 8 mol/l urea), guanidinium salt solutions (e.g., 6 mol/l guanidinium chloride), high concentration lithium salts (e.g., 4.5 mol/l lithium perchlorate). Chaotropic anions comprise the anions $F^-$, $PO_4^{3-}$, $SO_4^{2-}$, $CH_3COO^-$, $Cl^-$, and, for example, $BR^-$, $I^-$, $NO3^-$, $ClO_4^-$, $SCN^-$, and $Cl_3CCOO^-$. Chaotropic cations comprise the cations $Li^+$, $Mg^{2+}$, $Ca^{2+}$, $Ba^{2+}$, and for example the guanidinium isothiocyanate ($[CH_6N_3]^+SCN^-$) and guanidinium chloride. The chaotropic compounds may also aid in lysing cellular membranes and denaturing proteins.

In some embodiments, the method for extracting nucleic acids using the magnetic silica nanomembranes as disclosed herein further comprises at step b) contacting the sample with a sufficient amount of magnetic silica nanomembrane in the presence of an aqueous alcoholic solution such as ethanol or isopropanol. It is well-known that the aqueous alcoholic solution may help precipitate the nucleic acids from the other cellular or tissue components in the sample.

In some embodiments, the method for extracting the nucleic acids using the magnetic silica nanomembranes disclosed herein may comprise two, three, or more washing steps, such as at step e), for example. These washes can include buffers, alcohols, detergents, or other reagents known to be suitable for use in isolation and purification of nucleic acids.

For the purification of DNA, preference may be given to adding RNase in a biologically effective amount to the sample, whereby RNA can be digested and the intact DNA can be isolated from the sample. The RNase digestion can be carried out at different times during the extraction, at the earliest after lysis and at the latest after the elution at the end of the purification. However, in certain embodiments, detection of the DNA may be in the presence of the copurified RNA, i.e., by omitting the RNase step or by using buffer conditions that enable selective isolation of DNA with exclusion of the RNA.

For the isolation of RNA, preference may be given to adding DNase in a biologically effective amount to the sample. This may result in DNA being "digested" and going into solution, while the undigested RNA can be isolated from the solution. The DNase digestion can be carried out at different times during the extraction, at the earliest after lysis and at the latest after the elution at the end of the purification.

The methods as disclosed herein can be used to enrich a sample in a particular type of nucleic acid, e.g., DNA or RNA. For example, at step e), one can add a DNase to remove DNA from the nucleic acids in the sample and enrich the sample in RNA. Likewise, one can add an RNase to the sample at step e) to remove RNA from the nucleic acids in the sample and enrich the sample in DNA.

The methods as disclosed herein can be used to enrich a sample in a particular type of nucleic acid, e.g., DNA, RNA, long nucleic acids, or short nucleic acids. For example, during the binding step c) and washing step e), the percentage of alcohol in the buffers can be used to adjust solubility that will lead to preferred binding and elution of a specific species. Salts may also be used to preferentially extract a particular type of nucleic acid by adjusting the relative solubilities. Organic solvents may also be used to preferentially extract a particular type of nucleic acid by partitioning molecules of interest into different liquid phases.

In some embodiments, the method for extracting nucleic acids using the magnetic silica nanomembranes disclosed herein may comprise a drying step after step e).

In certain embodiments disclosed herein, the non-porous magnetic silica nanomembrane may harbor nucleic acid in a tethered conformation that enables the extraction of vast amounts of ultra high molecular weight (UHMW) nucleic acid by protecting the nucleic acid against fragmentation and bias binding away from a prone conformation. In contrast to microparticles and spin columns, where nucleic acids can be sheared by particle mixing or by flow through porous matrices, nucleic acids extracted with the magnetic silica nanomembranes disclosed herein can bind and release directly from the silica lamella without fragmentation. This gentle process ensures rapid isolation (such as, for example, less than about 1 hour) of high quality, Mb-sized nucleic acid, with minimal amounts of nucleic acid damage such as nicks and abasic sites, which can be used to generate high quality, long insert single molecule sequencing libraries.

For example, in certain embodiments, when the nucleic acids being extracted are long nucleic acids, the novel tentacle binding methods disclosed herein may capture ultra high molecular weight DNA up to a megabase in length and achieve binding capacities up to 1,000,000-times greater than silica microparticles. In certain embodiments, the process disclosed herein may be relatively fast, such as taking less than about 1 hour, less than about 45 minutes, less than about 30 minutes, less than about 15 minutes, or about 15 minutes. The ultra high molecular weight and low DNA damage that may result from the extraction methods disclosed herein may yield high quality sequencing libraries with single molecule mean read lengths of at least about 20 kb, such as at least about 50 kb, at least about 75 kb, at least about 100 kb, at least about 150 kb, at least about 200 kb, at least about 500 kb, or at least about 1 Mb.

It will be understood by those of ordinary skill in the art that the nucleic acids that are bound or adsorbed on the magnetic silica nanomembranes disclosed herein can be desorbed from the nanomembranes by the use of any elution solution known in the art. A typical elution solution can be a buffer comprising a mixture of (0.5M) ammonium acetate, 10 mM magnesium acetate and 1 mM EDTA, for example. Another typical elution solution can be a buffer comprising a mixture of 10 mM Tris base and 1 mM EDTA, for example. Yet another typical elution solution can be water.

In accordance with another embodiment, also disclosed herein are methods for extracting nucleic acids from formalin fixed paraffin embedded (FFPE) samples comprising: a) obtaining a FFPE sample comprising nucleic acids; b) deparaffinizing the sample; c) contacting the sample with a sufficient amount of magnetic silica nanomembranes; d) allowing the nucleic acids in the sample to adsorb onto the magnetic silica nanomembranes; e) moving the magnetic nanomembranes using a magnet; f) washing the magnetic silica nanomembranes to remove any non-nucleic acid components; and g) desorbing the nucleic acids from the magnetic silica nanomembranes to obtain the isolated and purified nucleic acids from the sample.

In certain embodiments disclosed herein, the FFPE tissue samples may be deparaffinized by adding an organic solvent, such as xylene. The xylene is then removed and the sample pellet is washed with graded ethanol solutions to eliminate xylene and rehydrate the DNA. In other embodiments, the deparaffinization methods can be varied by altering the xylene concentration, incubation times, and wash protocol to ensure that all the paraffin is removed and xylene carry through is minimal. FFPE tissue samples may also contain DNA that has been highly cross-linked. In some embodiments, reversal of cross-linking may be performed by heating, such as to a temperature of about 95° C. In other embodiments, this reversal may be performed chemically. After deparaffinization and cross-linking reversal, nucleic acid extraction is performed using a process as outlined above.

It will also be understood by those of ordinary skill in the art that the compositions, devices, and methods using the magnetic silica nanomembranes disclosed herein can be combined with any other analytic techniques useful for isolating, purifying and analyzing nucleic acids known in the art.

In accordance with certain embodiments, disclosed herein is a kit comprising one or more magnetic silica nanomembranes and instructions for use of the magnetic silica nanomembranes for isolation or purification of nucleic acid, such as DNA or RNA, from a sample. Such a kit may be provided in a container with other reagents or materials necessary to perform the nucleic acid isolation and purification. The kits disclosed herein can also include a device or apparatus comprising the magnetic silica nanomembranes.

In one embodiment, the magnetic nanomembrane is used for DNA extraction from a cell sample. The cell sample may first be trypsinized, added to a container, and resuspended in a buffer solution, such as phosphate-buffered saline (PBS).

The cell sample may then be lysed. Lysing of the sample may comprise breaking open of the cells or cellular structures in the sample by any means known in the art. Lysis may comprise, for example, mechanical lysis methods such as ultrasound or bead beating, thermal lysis (e.g., freeze-thaw cycles or heating the sample), and chemical lysis (e.g., with detergents or enzymes). In certain embodiments, a lysing buffer may then be added to the cells. In certain embodiments, the lysing buffer may comprise proteinase K, guanidine hydrochloride, and Triton X-100, for example.

After lysis, a magnetic silica nanomembrane as disclosed herein may be added to the lysed cells to enable nucleic acid binding to the magnetic nanomembranes. Additionally, in certain embodiments, isopropyl alcohol may be added to the solution. In other embodiments, ethyl alcohol may be added to the solution. After binding, a magnet may be used to pull the magnetic silica nanomembrane to a side of the container such that the lysing buffer and unbound cellular impurities can be pipetted out.

A wash buffer may then added to the container and the magnet released to enable the wash solution to adequately contact the nanomembrane. In certain exemplary embodiments, the wash buffer may comprise, for example, isopropyl alcohol or ethyl alcohol. In other embodiments, the wash solution may contain chaotropic salts. The magnet may also be used to draw the nanomembrane aside to pipette out the wash solution, and the wash may be repeated multiple times, such as two, three, or four times. This series of wash steps may act as stringency washes.

After the final wash, an elution buffer may be added to the container and the magnet released. In certain embodiments, the container may be incubated to enable the DNA to release, or desorb, from the nanomembrane. Finally, the magnet may again be applied to pull the nanomembrane aside so that the purified DNA may be pipetted out.

The low shear, planar, non-porous format of the magnetic silica nanomembranes disclosed herein enables extraction of large genomic fragments with length exceeding about 100 kb, such as greater than about 250 kb, greater than about 500 kb, greater than about 1 Mb, greater than about 5 Mb, or greater than about 10 Mb.

In certain embodiments disclosed herein, a permanent magnet or electromagnet may be used.

In some embodiments, the binding and wash buffers may comprise high levels of isopropyl alcohol (70%) or ethyl alcohol (70%), as well as high levels of chaotropic salts such as guanidine hydrochloride (6 M), guanidine thiocyanate (6 M), sodium perchloride (4 M), or sodium iodide (4 M) to facilitate nucleic acid binding to the silica nanomembrane and removal of contaminating salts, proteins, lipids, etc.

In certain embodiments, the extraction buffers may have components that are incompatible with the magnetic materials and lead to degradation or leaching into solution. Accordingly, in one embodiment, the extraction buffers may be optimized to remain chemically compatible with the magnetic materials. In another embodiment, a passivating layer may be used to protect the magnetic material from attack.

In another embodiment, the magnetic silica nanomembrane is used for automated nucleic acid extraction in conjunction a robotic extraction system. Robotic extraction systems may include, for example, pipetting type instruments such as the Qiagen QIAsymphony, Qiagen Biorobot, Tecan Freedom EVO, and Beckman Coulter Biomek workstation and magnetic rod type instruments such as the Thermo Scientific KingFisher and Perkin Elmer Chemagic.

In some embodiments, multiple pieces of magnetic silica nanomembrane may be used in a single extraction tube.

In accordance with yet another embodiment, the magnetic silica nanomembranes can be used in a microfluidic chip format. The microfluidic chip is an apparatus that, in certain embodiments, comprises a solid substrate comprising a plurality of discrete magnetic silica nanomembranes regions. The magnetic silica nanomembranes may be located at spatially defined addresses on the substrate. The magnetic silica nanomembranes may be attached to the chip in a wide variety of ways or confined within certain regions of the chip, as will be appreciated by those in the art. The magnetic silica nanomembranes may either be synthesized first, with subsequent attachment or confinement to the chip, or may be directly synthesized on the chip or as part of the chip

EXAMPLES

Example 1—Magnetic Nanomembrane Fabrication

Figure 13:
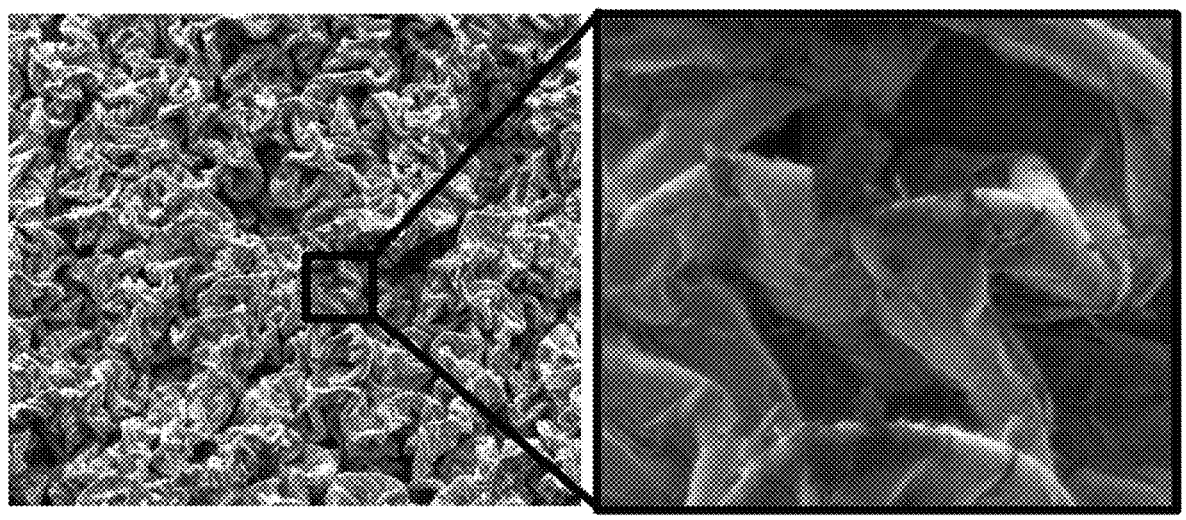
FIG. 13 is a scanning electron microscope (SEM) image illustrating the surface topology of a magnetic silica nanomembrane. The inset shows a region at higher magnification.

A 20 μm thick polyolefin film was coated on one side with a 100 nm thick layer of silicon dioxide using e-beam evaporation. The other side of the polyolefin film was then alternately coated with a 20 nm thick layer of silicon dioxide, a 30 nm thick layer of iron, and a 20 nm thick layer of silicon dioxide using e-beam evaporation. The coated polyolefin substrate was then heat shrunk in an oven at 300° F. for 3 minutes. This created a nanomembrane with micro- and nanoscale silica lamella on both sides. The backside silica lamella comprised a magnetic iron center sandwiched by silica such that magnetic manipulation could be performed and nucleic acids could bind or adsorb to both sides of the magnetic nanomembrane. The silica enveloping both sides of the iron acts as a binding surface for nucleic acids and protects the iron from reacting with buffer components. FIG. 2 is a flow chart illustrating the exemplary fabrication process. FIG. 13 shows an SEM image of the surface topology for the magnetic silica nanomembrane, showing the microscale and nanoscale silica structures, such as flakes, lamella, wrinkles, and folds. The inset on the right shows a region at a higher magnification.

Example 2—Magnetic Nanomembrane Extraction Process with MCF-7 Cells

Figure 4:
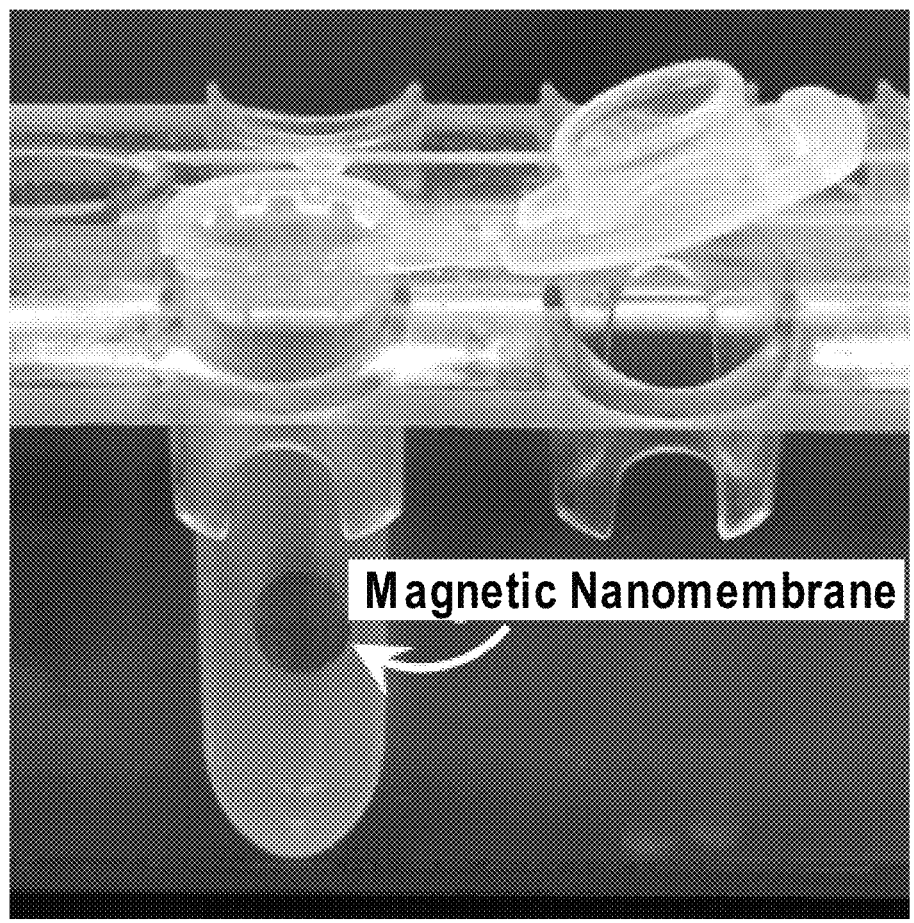
FIG. 4 is a photograph of a magnetic nanomembrane disc being attracted to the side of a microcentrifuge tube using a magnet.

The magnetic silica nanomembrane fabricated in Example 1 above was used for DNA extraction from $2 \times 10^6$ MCF-7 cultured cells. The cultured cells were trypsinized and resuspended in a phosphate buffer saline (PBS) solution. A lysing buffer comprising proteinase K, guanidine hydrochloride, and Triton X-100 was then added to the cells and incubated for 1 hour. Then the magnetic silica nanomembrane and isopropyl alcohol were added to the lysed cells to enable nucleic acid binding to the magnetic silica nanomembrane. A magnet was then used to pull the magnetic nanomembrane to the side of the microcentrifuge tube such that the lysing buffer and unbound cellular impurities could be pipetted out. FIG. 4 shows a photograph of a magnetic nanomembrane being pulled to the side of a microcentrifuge tube using a magnetic rack. A wash buffer containing 70% EtOH was then added to the tube, and the magnet was released to enable the wash solution to adequately contact the nanomembrane. The magnet was then used to draw the nanomembrane aside so that the wash solution could be pipetted out. The wash was repeated two more times.

Figure 5:
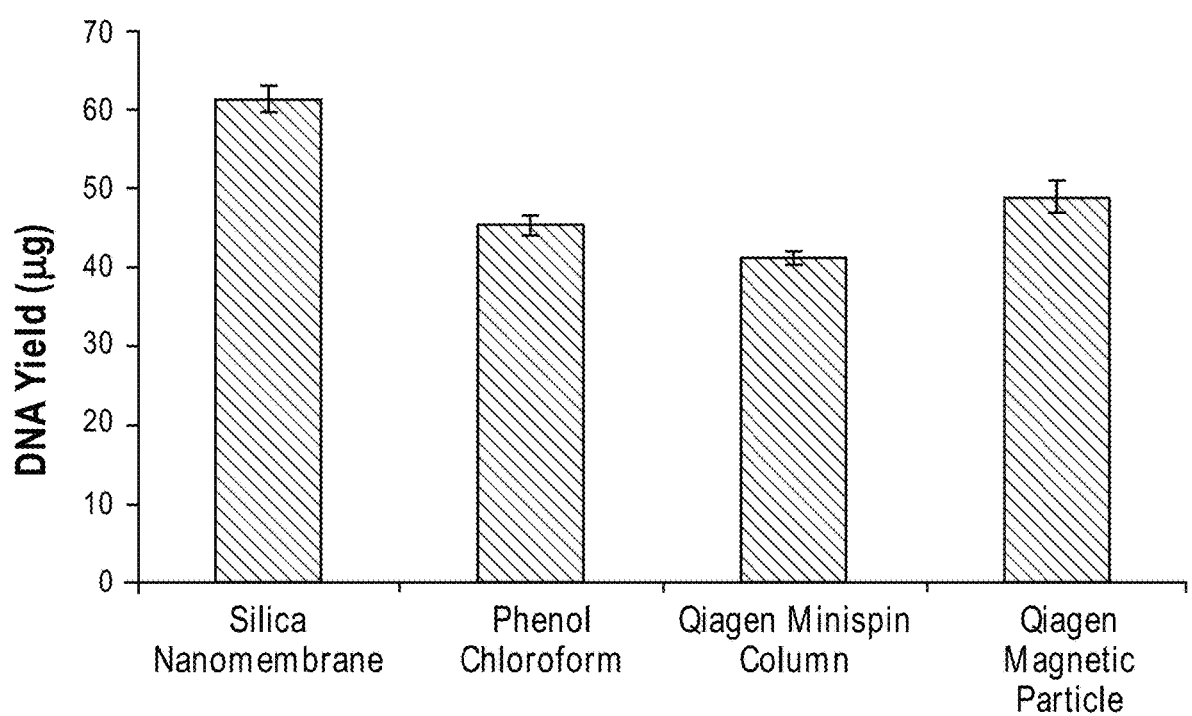
FIG. 5 is a bar graph comparing the DNA yield for extraction using a magnetic silica nanomembrane versus phenol-chloroform, Qiagen Minispin column, and Qiagen magnetic particle technology.

After the third wash, the elution buffer was added to the tube and the magnet was then released. The tube was incubated for 15 minutes to enable the DNA to release, or desorb, from the nanomembrane. Finally, the magnet was applied again to pull the nanomembrane aside, and the purified DNA was pipetted out. 61 μg of DNA was recovered as measured by PicoGreen® assay. In comparison, DNA extraction of $2 \times 10^6$ MCF-7 cultured cells using phenol-chloroform recovered 45 μg of DNA, a Qiagen Minispin Column recovered 41 μg of DNA, and DNA extraction from Qiagen magnetic particle technology recovered 49 μg of DNA. FIG. 5 is a bar graph showing the results of the magnetic silica nanomembrane DNA extraction in comparison to DNA extraction using phenol-chloroform, Qiagen Minispin column, and magnetic particle technology. As shown in FIG. 5, the magnetic silica nanomembrane was able to extract a higher yield of DNA.

Figure 6:
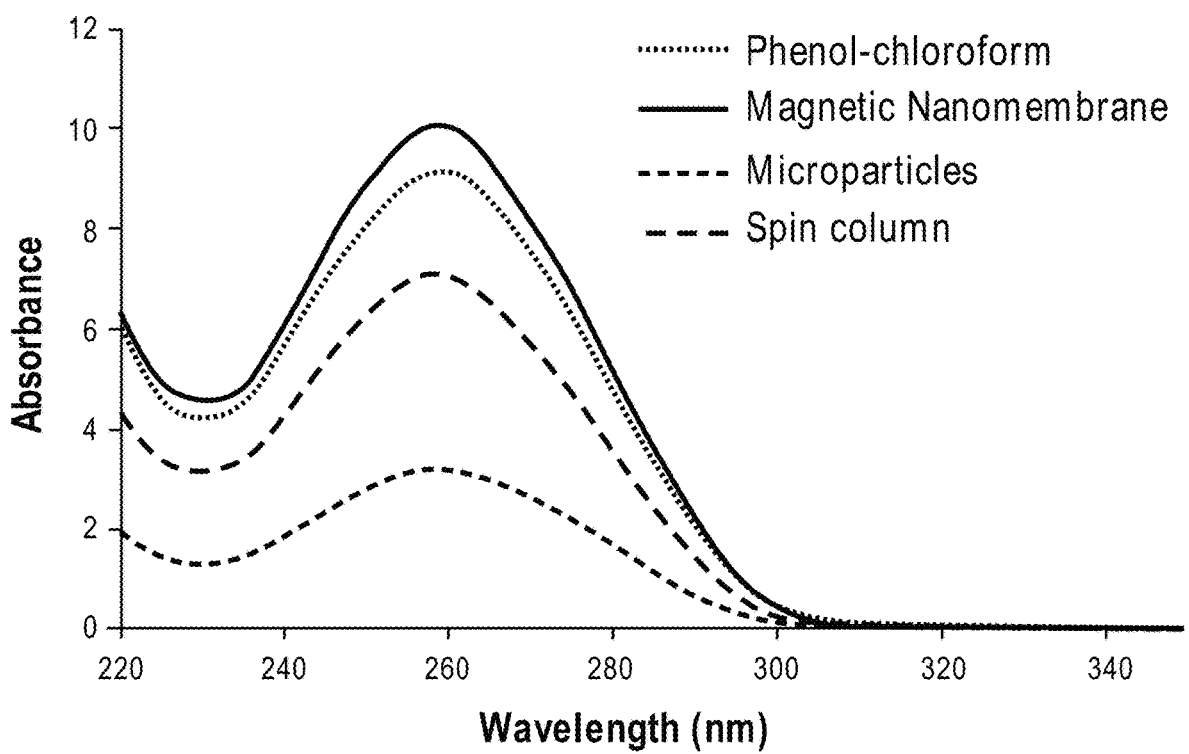
FIG. 6 is a graph illustrating the UV absorbance versus the wavelength for DNA extracted from MCF-7 cells using phenol chloroform, magnetic silica nanomembrane, magnetic bead microparticles, and a spin column.

The purity of the extracted DNA from all of the extraction methods was measured with a spectrophotometer using UV absorbance. The purity of the extracted DNA was comparable for all four methods. The DNA extracted using phenol-chloroform had high purity with 260/230 and 260/280 ratios of 1.91 and 2.15, respectively. The DNA extracted using the magnetic silica nanomembrane also had a very high purity with 260/280 and 260/230 of 1.96 and 2.16, respectively. The DNA extracted with magnetic bead microparticles had a purity with 260/280 and 260/230 of 1.99 and 2.23, respectively, while the DNA extracted with the spin column had a purity with 260/280 and 260/230 of 1.89 and 2.16, respectively. FIG. 6 is a graph illustrating the UV absorbance versus the wavelength, and Table 1 below shows the purity results of the UV absorbance for all four methods of DNA extraction analyzed.

TABLE 1

| Extraction Method | 260/280 | 260/230 |
| --- | --- | --- |
| Phenol-Chloroform | 1.91 | 2.15 |
| Nanomembrane | 1.96 | 2.16 |
| Microparticle | 1.99 | 2.23 |
| Spin column | 1.89 | 2.16 |

Figure 7:
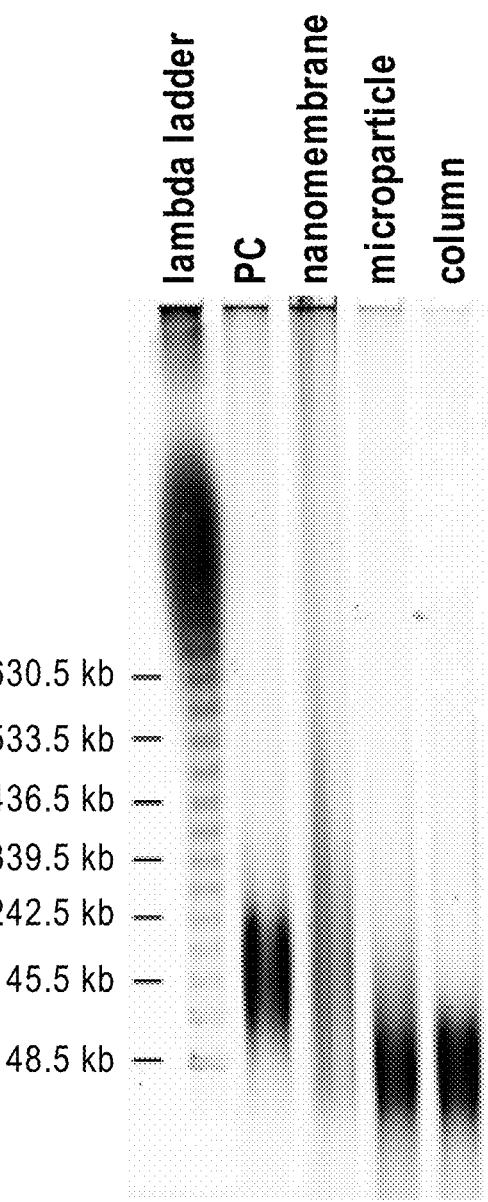
FIG. 7 is a pulsed field gel image illustrating the size of genomic DNA extracted from MCF-7 cells using phenol chloroform, magnetic silica nanomembrane, magnetic bead microparticles, and a spin column.

The DNA extracted from the nanomembrane, phenol-chloroform, spin column, and magnetic beads was subjected to pulsed field gel electrophoresis for comparison of DNA size, and the pulsed field gel electrophoresis image is shown in FIG. 7. As shown in FIG. 7, the low shear, planar, non-porous format of the nanomembrane enabled extraction of genomic fragments of DNA having lengths exceeding 100 kb with some lengths exceeding 300 kb.

Example 3—Magnetic Nanomembrane Extraction Process with Whole Human Blood

A magnetic silica nanomembrane fabricated according to the method disclosed above in Example 1 was used to extract DNA from whole human blood. A lysing buffer comprising proteinase K, guanidine hydrochloride, and Triton X-100 was added to 100 μL of blood and incubated for 1 hour. Then the magnetic silica nanomembrane and isopropyl alcohol were added to the lysed cells to enable nucleic acid binding to the magnetic silica nanomembrane. A magnet was then used to pull the magnetic nanomembrane to the side of the microcentrifuge tube such that the lysing buffer and unbound cellular impurities could be pipetted out. A wash buffer containing 70% EtOH was then added to the tube, and the magnet was released to enable the wash solution to adequately contact the nanomembrane. The magnet was then used to draw the nanomembrane aside so that the wash solution could be pipetted out. The wash was repeated two more times.

Figure 8:
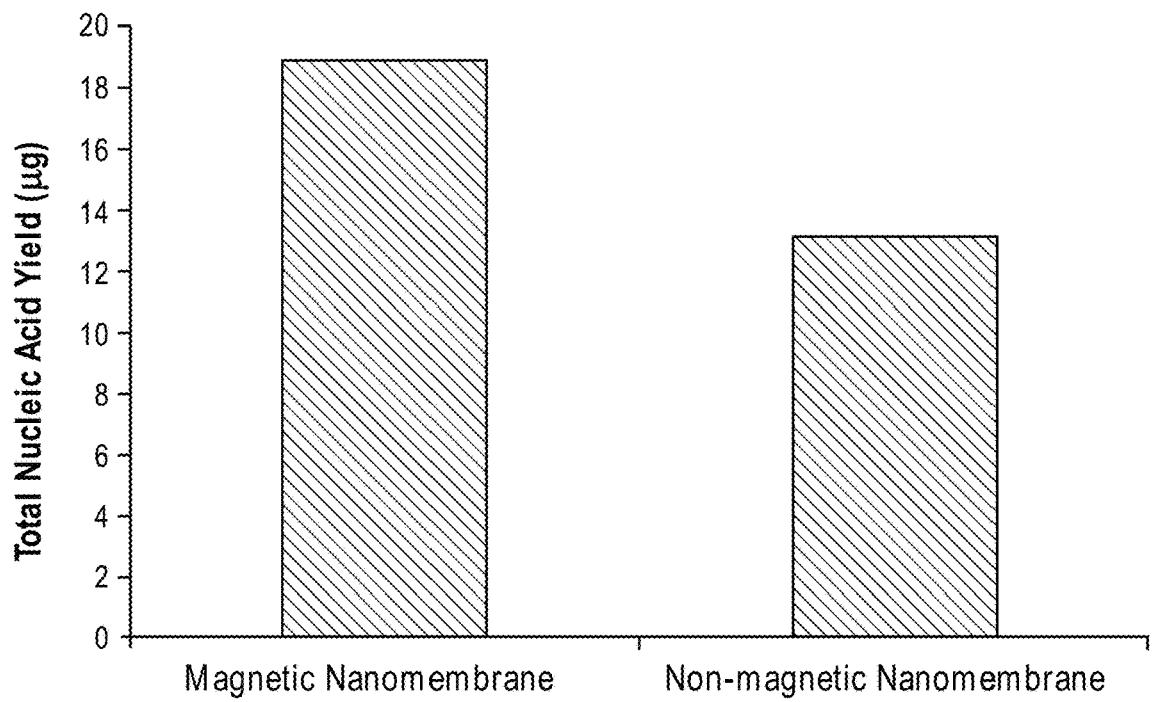
FIG. 8 is a bar graph illustrating the yield for total nucleic acid extracted from whole human blood using a magnetic nanomembrane and a non-magnetic nanomembrane.

After the third wash, the elution buffer was added to the tube and the magnet was then released. The tube was incubated for 15 minutes to enable the DNA to release, or desorb, from the nanomembrane. Finally, the magnet was applied again to pull the nanomembrane aside, and the purified DNA was pipetted out. The magnetic nanomembrane extracted 18.9 μg of total nucleic acid (DNA+RNA). As shown in FIG. 8, a bar graph comparing the quantity of total nucleic acid extracted from the magnetic nanomembrane versus a nonmagnetic nanomembrane, the nucleic acid yield using the magnetic nanomembrane is comparable to a non-magnetic nanomembrane, indicating that the presence of the magnetic layer does not adversely affect the extraction efficiency.

Figure 11:
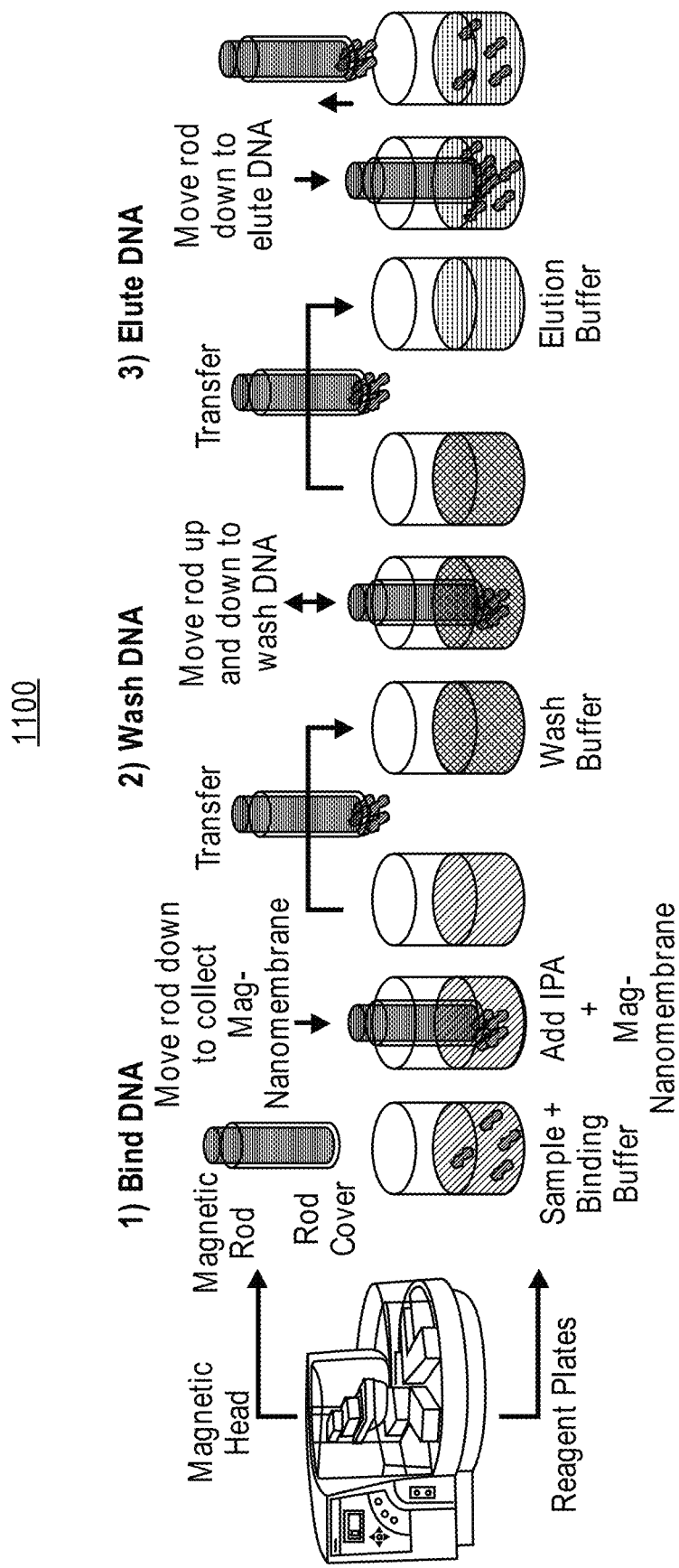
FIG. 11 is a schematic illustration of automated DNA extraction using a magnetic nanomembrane and a magnetic rod actuated instrument.

Example 4—Automated Magnetic Nanomembrane Extraction Process with KingFisher™ Duo Prime Automated extraction was performed on a Thermo Scientific KingFisher™ Duo Prime. Rather than using a magnet to hold the magnetic nanomembrane and pipetting solutions in and out of the tube as in FIG. 3, the KingFisher™ Duo Prime extracts DNA using a magnetic head comprising an array of magnetic rods to transfer magnetic nanomembranes from one solution to the next as shown in FIG. 11. As illustrated in a method 1100 in FIG. 11, actuating the magnetic rod in and out of solution enables the magnetic nanomembrane to be transferred from one buffer to the next. Pulling the magnetic rod out of the plastic rod cover enables the magnetic nanomembrane to be released into solution to facilitate washing and mixing. In this manner, DNA extraction can be performed by successively transferring the magnetic nanomembrane into the binding buffer to capture the lysed DNA, then into the wash buffers to rinse away salt and impurities, and finally into the elution buffer to elute the DNA and remove the used magnetic nanomembrane. The wash steps may be skipped to speed processing. See, for example, FIG. 11.

Figure 9:
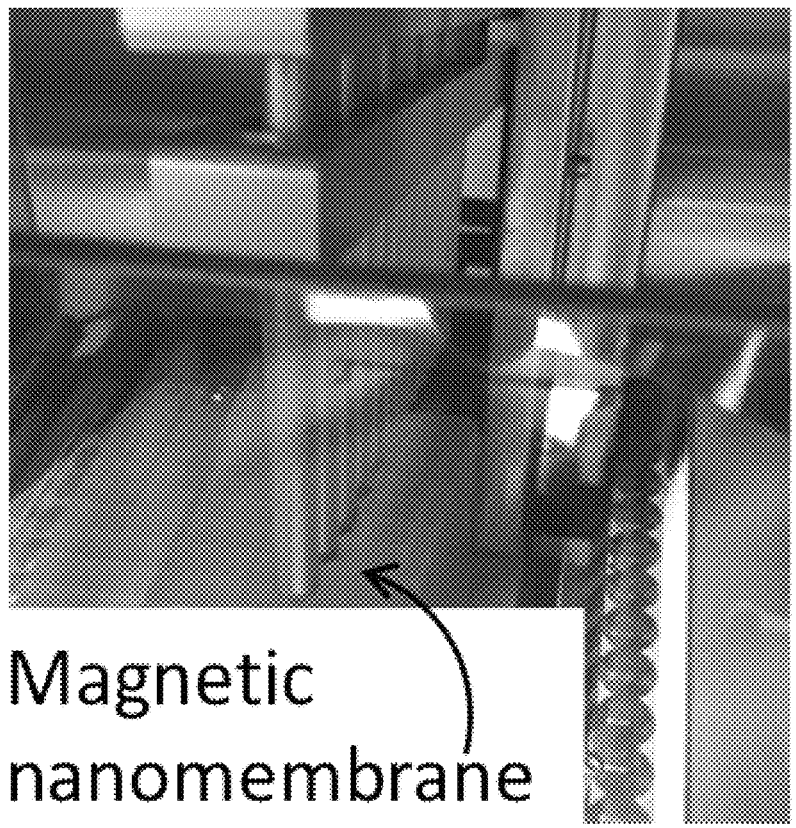
FIG. 9 is a photograph showing magnetic nanomembranes captured by the magnetic rods on the robotic arm of a Thermo Scientific KingFisher™ Duo Prime automated DNA extraction system.
Figure 12:
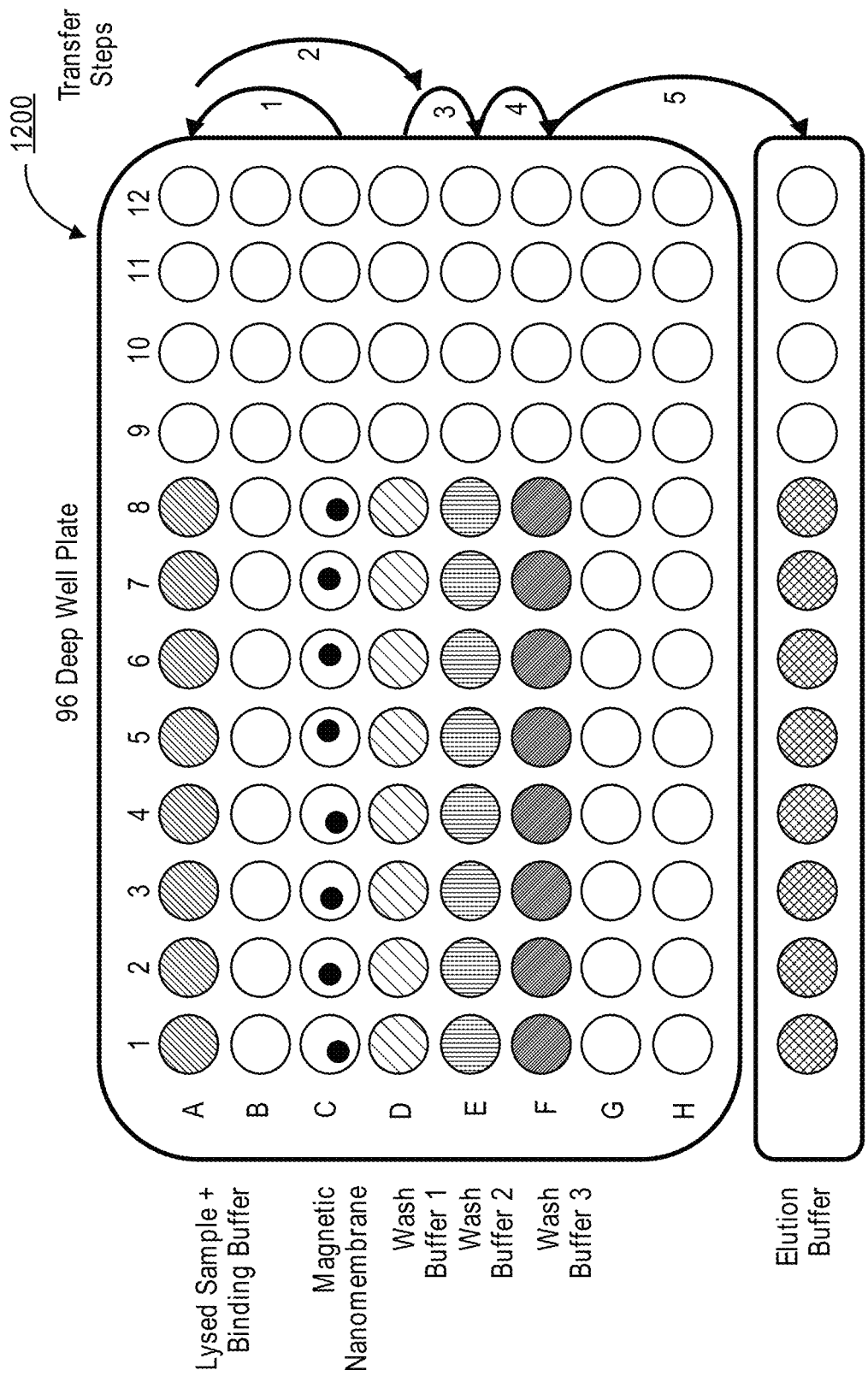
FIG. 12 is a schematic illustration of an exemplary transfer of magnetic nanomembranes between solutions in an automated DNA extraction using a magnetic rod actuated instrument.

Automated DNA extraction from MCF-7 cells was performed on a Thermo Scientific KingFisher™ Duo Prime. Eight samples were run simultaneously using the robotic extraction system. The cultured cells were trypsinized and resuspended in a phosphate buffer saline (PBS) solution. As depicted in FIG. 12, the $1\times10^6$ cells where placed into seven separate wells of row A of a 96 deep well plate 1200. Eight individual magnetic nanomembranes were added to wells of row C, wash buffers were added to rows D, E, and F, and elution buffer was added to the elution strip. See, for example, FIG. 12. A lysing buffer comprising proteinase K, guanidine hydrochloride, and Triton X-100 was then added to the sample wells (row A) and incubated for 10 minutes with gentle mixing. Isopropanol was manually added to each of the wells in row A. The KingFisher™ robotic arm comprising a series of magnetic rods then captured the magnetic nanomembranes from row C and moved them to row A to contact them with the sample, enabling the DNA to adsorb to the magnetic nanomembrane. FIG. 9 is a photograph showing the magnetic nanomembranes captured by the head comprising an array of magnetic rods on the robotic arm. The robotic arm then moved the magnetic nanomembrane sequentially through wash buffers in rows D, E, and F, as depicted in FIG. 12.

Figure 10:
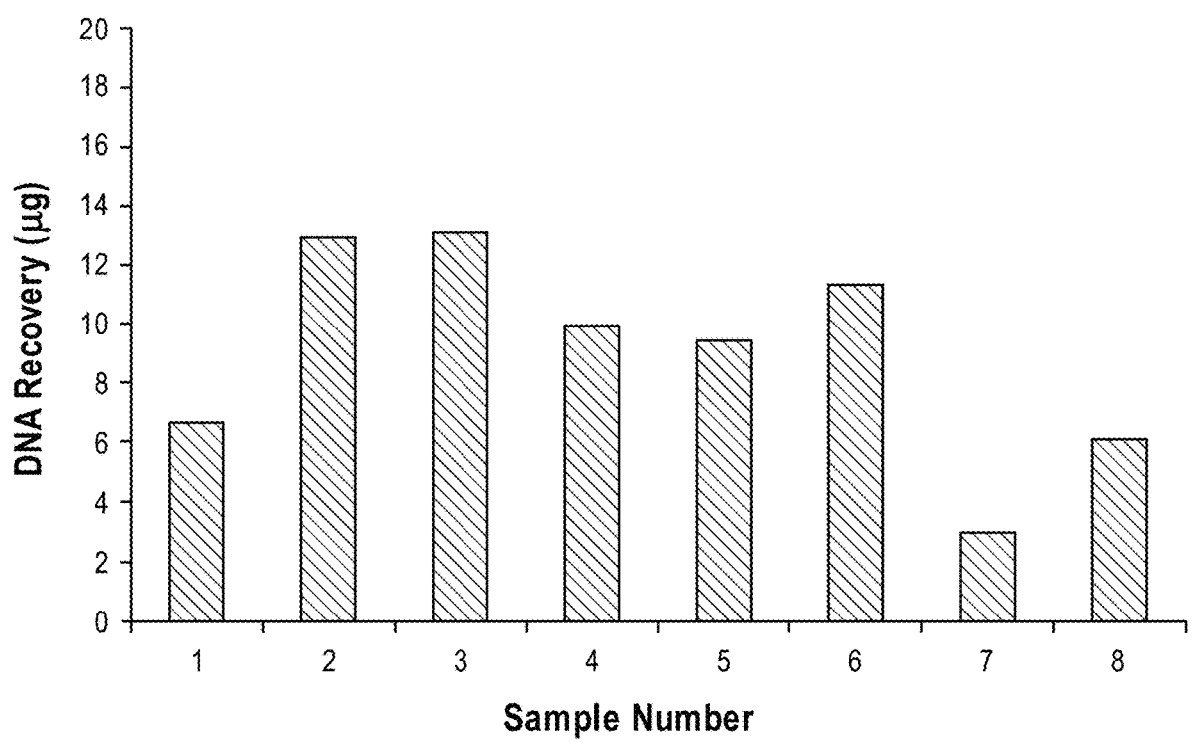
FIG. 10 is a bar graph showing the DNA recovery from eight samples run on an automated DNA extraction system.

After the third wash, the robotic arm moved the magnetic nanomembrane to the elution buffer to elute the adsorbed DNA. The magnetic nanomembranes were then removed by the robotic arm, leaving the purified DNA behind. The amount of DNA recovered from each of the eight samples using the automated DNA extraction system is shown in the column chart of FIG. 10. The DNA yield using the automated extraction system was 9.1±3.5 μg.

What is claimed is:

1. A method of fabricating a magnetic silica nanomembrane, the method comprising:
    coating at least a first surface of a thermoplastic polymer substrate with at least a first non-porous silica layer or with at least a first magnetic component, wherein when the first surface of the thermoplastic polymer substrate is coated with the first non-porous silica layer, the method further comprises coating the first non-porous silica layer and/or a second surface of the thermoplastic polymer substrate with at least a first magnetic component to produce a coated thermoplastic polymer substrate, and wherein when the first surface of the thermoplastic polymer substrate is coated with the first magnetic component, the method further comprises coating the first magnetic component and/or a second surface of the thermoplastic polymer substrate with at least a first non-porous silica layer to produce a coated thermoplastic polymer substrate; and,
    heating the coated thermoplastic polymer substrate at a temperature and a duration to reduce a size of the coated thermoplastic polymer substrate sufficient for at least the first non-porous silica layer to form at least one surface morphology chosen from a plurality of (a) microscale silica structures and (b) nanoscale silica structures.

2. The method of claim 1, wherein a size of the coated thermoplastic polymer substrate reduces to between about 0.1% to about 95% of an original size of the coated thermoplastic polymer substrate.

3. The method of claim 1, wherein the thermoplastic polymer substrate is selected from the group consisting of: polymethyl methacrylate, polycarbonate, polystyrene, cyclic polyolefin polymers, polypropylene, polyvinyl chloride, polyethylene, fluorinated ethylene propylene, polytetrafluoroethylene, and polyvinylidene fluoride.

4. The method of claim 1, wherein the non-porous silica layer comprises a thickness ranging from about 2 nm to about 500 nm thick prior to heating the coated thermoplastic polymer substrate.

5. The method of claim 1, wherein the non-porous silica layer comprises silicon dioxide.

6. The method of claim 1, wherein at least one magnetic material is embedded within the thermoplastic polymer substrate.

7. The method of claim 1, wherein the thermoplastic polymer substrate is magnetic.

8. The method of claim 1, wherein the first magnetic component is selected from the group consisting of: diamagnetic materials, paramagnetic materials, ferrimagnetic materials, and ferromagnetic materials.

9. The method of claim 1, wherein the first magnetic component is selected from the group consisting of: iron, nickel, cobalt, magnetite, hematite, maghemite, steel, alnico, permalloy, alperm, fernico, sendust, and cunife.

10. The method of claim 1, wherein the first magnetic component has a thickness ranging from about 5 nm to about 10 µm thick prior to heating the coated thermoplastic polymer substrate.

11. The method of claim 1, wherein the surface morphology is selected from the group consisting of: flakes, lamella, wrinkles, and folds.

12. The method of claim 1, further comprising one or more additional non-porous silica layers and/or magnetic components disposed over the coated thermoplastic polymer substrate.

13. The method of claim 1, further comprising a passivation layer disposed over the coated thermoplastic polymer substrate.

14. The method of claim 1, wherein the first non-porous silica layer is deposited using a deposition method chosen from electron beam evaporation, sputtering, chemical vapor deposition, plasma enhanced chemical vapor deposition, electroplating, atomic layer deposition, chemical solution deposition, and spin coating.

15. The method of claim 1, wherein the magnetic silica nanomembrane further comprises a surface functionalization that is selected from the group consisting of: aminopropyl groups, chloropropyl groups, octadecyl groups, octyl groups, quaternary ammonium groups, diethylaminoethyl group, sulfonic acid groups, phenyl groups, polyethylene glycol, lipids, chitosan, biotin, streptavidin, antibodies, proteins, and enzymes.

16. The method of claim 1, further comprising cutting the coated thermoplastic polymer substrate to a shape of a disk having a diameter of from about 1 mm to about 6 mm.

17. The method of claim 1, wherein the magnetic silica nanomembrane is configured to be manipulated by a magnetic force.

18. A method of fabricating a magnetic silica nanomembrane, the method comprising:
forming a first magnetic component onto a first surface of a thermoplastic polymer substrate;
coating the first magnetic component with a first non-porous silica layer;
coating a second surface of the of the thermoplastic polymer substrate with a second non-porous silica layer to produce a coated thermoplastic polymer substrate; and
heating the coated thermoplastic polymer substrate at a temperature and a duration to reduce a size of the coated thermoplastic polymer substrate sufficient for the first non-porous silica layer or the second non-porous silica layer to form at least one surface morphology chosen from a plurality of (a) microscale silica structures and (b) nanoscale silica structures.

19. The method of claim 18, further comprising:
coating the second surface of the thermoplastic polymer substrate with a third non-porous silica layer prior to forming the first magnetic component onto the first surface of a thermoplastic polymer substrate.

20. The method of claim 18, wherein the non-porous silica layer comprises silicon dioxide.

21. The method of claim 18, wherein the surface morphology is selected from the group consisting of: flakes, lamella, wrinkles, and folds.

22. The method of claim 18, wherein the magnetic silica nanomembrane is configured to be manipulated by a magnetic force.

* * * * *